United States Patent
Kajiwara et al.

(10) Patent No.: US 10,893,224 B2
(45) Date of Patent: Jan. 12, 2021

(54) IMAGING ELEMENT AND ELECTRONIC DEVICE

(71) Applicant: SONY CORPORATION, Tokyo (JP)

(72) Inventors: Yuu Kajiwara, Kanagawa (JP); Masahiko Nakamizo, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/077,173

(22) PCT Filed: Feb. 14, 2017

(86) PCT No.: PCT/JP2017/005203
§ 371 (c)(1),
(2) Date: Aug. 10, 2018

(87) PCT Pub. No.: WO2017/150168
PCT Pub. Date: Sep. 8, 2017

(65) Prior Publication Data
US 2019/0052828 A1 Feb. 14, 2019

(30) Foreign Application Priority Data
Feb. 29, 2016 (JP) .................. 2016-037208

(51) Int. Cl.
*H04N 5/3745* (2011.01)
*H01L 27/146* (2006.01)
(Continued)

(52) U.S. Cl.
CPC ... *H04N 5/37457* (2013.01); *H01L 27/14603* (2013.01); *H01L 27/14641* (2013.01);
(Continued)

(58) Field of Classification Search
CPC .. H04N 5/3559; H04N 5/37457; H04N 5/357; H04N 5/359–3658;
(Continued)

(56) References Cited

U.S. PATENT DOCUMENTS

| 2011/0181747 A1 | 7/2011 | Kido et al. |
| 2013/0049082 A1* | 2/2013 | Kato .................. H04N 5/3745 257/292 |

(Continued)

FOREIGN PATENT DOCUMENTS

| CN | 102157536 A | 8/2011 |
| JP | 2011-155596 A | 8/2011 |

(Continued)

OTHER PUBLICATIONS

International Search Report and Written Opinion of PCT Application No. PCT/JP2017/005203, dated May 16, 2017, 07 pages of ISRWO.

*Primary Examiner* — Paul M Berardesca
(74) *Attorney, Agent, or Firm* — Chip Law Group

(57) ABSTRACT

The present technology relates to an imaging element and an electronic device that enable pixels to flexibly share a charge voltage converting unit. The imaging element includes a pixel array unit in which pixels respectively having charge voltage converting units and switches are arranged, and the charge voltage converting units of the plurality of pixels are connected to a signal line in parallel via the respective switches. The present technology is applied to, for example, a Complementary Metal Oxide Semiconductor (CMOS) image sensor in which pixels share a charge voltage converting unit.

7 Claims, 16 Drawing Sheets

(51) Int. Cl.
  *H04N 5/355* (2011.01)
  *H04N 5/347* (2011.01)
  *A61B 1/04* (2006.01)
  *A61B 1/313* (2006.01)
  *B60R 1/00* (2006.01)
  *G05D 1/02* (2020.01)
  *H04N 5/341* (2011.01)

(52) U.S. Cl.
  CPC ....... *H01L 27/14643* (2013.01); *H04N 5/347* (2013.01); *H04N 5/3559* (2013.01); *A61B 1/041* (2013.01); *A61B 1/042* (2013.01); *A61B 1/3132* (2013.01); *B60R 1/00* (2013.01); *B60R 2300/105* (2013.01); *G05D 1/0246* (2013.01); *H04N 5/341* (2013.01)

(58) Field of Classification Search
  CPC ....... H04N 5/374–37457; H04N 5/347; H04N 5/361–3675; H01L 27/14603; H01L 27/14641
  See application file for complete search history.

(56) References Cited

U.S. PATENT DOCUMENTS

| | | | |
|---|---|---|---|
| 2013/0214128 A1* | 8/2013 | Yamashita | H01L 27/14609 250/208.1 |
| 2014/0333812 A1 | 11/2014 | Kuroda | |
| 2015/0146060 A1* | 5/2015 | Suzuki | H04N 5/3559 348/300 |
| 2016/0373668 A1* | 12/2016 | Komai | H04N 5/347 |
| 2017/0187969 A1* | 6/2017 | Kitamori | H04N 5/37457 |
| 2018/0027192 A1* | 1/2018 | Morisaki | H04N 5/347 348/308 |
| 2018/0054578 A1* | 2/2018 | Kitamori | H04N 5/37457 |
| 2018/0149831 A1* | 5/2018 | Kitamori | G02B 7/30 |

FOREIGN PATENT DOCUMENTS

| | | | | |
|---|---|---|---|---|
| JP | 2014-217021 A | 11/2014 | | |
| JP | 2014-220642 A | 11/2014 | | |
| WO | WO-2016129408 A1 * | 8/2016 | | H04N 5/347 |

* cited by examiner

IMAGING ELEMENT AND ELECTRONIC DEVICE

CROSS REFERENCE TO RELATED APPLICATIONS

This application is a U.S. National Phase of International Patent Application No. PCT/JP2017/005203 filed on Feb. 14, 2017, which claims priority benefit of Japanese Patent Application No. JP 2016-037208 filed in the Japan Patent Office on Feb. 29, 2016. Each of the above-referenced applications is hereby incorporated herein by reference in its entirety.

TECHNICAL FIELD

The present technology relates to an imaging element and an electronic device, and particularly, to an imaging element and an electronic device suitable for a case where pixels share a charge voltage converting unit.

BACKGROUND ART

Conventionally, an imaging element has been proposed in which pixel adjacent to each other in the vertical direction can share a charge voltage converting unit via a coupling transistor (for example, refer to Patent Document 1).

CITATION LIST

Patent Document

Patent Document 1: Japanese Patent Application Laid-Open No. 2014-217021

SUMMARY OF THE INVENTION

Problems to be Solved by the Invention

However, in the invention disclosed in Patent Document 1, since a coupling transistor is connected to a signal line for connecting charge voltage converting units of pixels in the vertical direction, there is a case where the pixels cannot share the charge voltage converting unit.

For example, in a case where a failure such as a white point and a dark current occurs in a certain pixel, if the charge voltage converting unit of the pixel in which the failure occurs is shared with the other pixel, the failure affects the other pixel. Therefore, it is necessary to turn off the coupling transistor between the pixel in which the failure occurs and a pixel adjacent to that pixel in the vertical direction and separate the pixel in which the failure occurs from the other pixels. However, if the pixel in which the failure occurs is separated, the charge voltage converting unit cannot be shared between a pixel arranged on the upper side of the pixel in which the failure occurs along the vertical direction and a pixel arranged on the lower side of the pixel in which the failure occurs along the vertical direction.

Therefore, according to the present technology, the pixels can flexibly share the charge voltage converting unit.

Solutions to Problems

An imaging element according to a first aspect of the present technology includes a pixel array unit in which pixels respectively having charge voltage converting units and switches are arranged, and the charge voltage converting units of the plurality of pixels are connected to a signal line in parallel via the respective switches.

The signal line can extend in a direction in which the pixels are aligned in the pixel array unit.

In the pixel, pixel transistors can be substantially symmetrically arranged in at least one direction of the alignment directions of the pixels in the pixel array unit.

The pixel includes a plurality of photoelectric conversion elements and a plurality of transfer transistors that transfers an electric charge generated by each photoelectric conversion element to the charge voltage converting unit, and in the pixel, the plurality of transfer transistors can be substantially symmetrically arranged in the same direction as the pixel transistors.

The pixel transistor can include a reset transistor used to reset the charge voltage converting unit, an amplification transistor used to amplify a voltage of the charge voltage converting unit, and a coupling transistor configuring the switch.

The pixel transistor can further include a selection transistor used to select the pixel.

An electronic device according to a second aspect of the present technology includes an imaging element that includes a pixel array unit in which pixels respectively having charge voltage converting units and switches are arranged, and in which, charge voltage converting units of the plurality of pixels are connected to a signal line in parallel via the respective switches and a signal processing unit that performs processing on a signal of the imaging element.

In the first or second aspect of the present technology, the charge voltage converting units of the plurality of pixels are shared via the switch of each pixel and the signal line.

Effects of the Invention

According to the first or second aspect of the present technology, the pixels can flexibly share the charge voltage converting unit.

Note that the effects described herein are not necessarily limited and that the effect may be any effects described in the present disclosure.

MODE FOR CARRYING OUT THE INVENTION

An embodiment for carrying out the invention (referred to as "embodiment" below) will be described in detail with reference to the drawings. Note that, the description will be made in the following order.

1. Embodiment
2. Modification
3. Exemplary Usage of Imaging Element

1. Embodiment

[Basic System Configuration]

Figure 1:
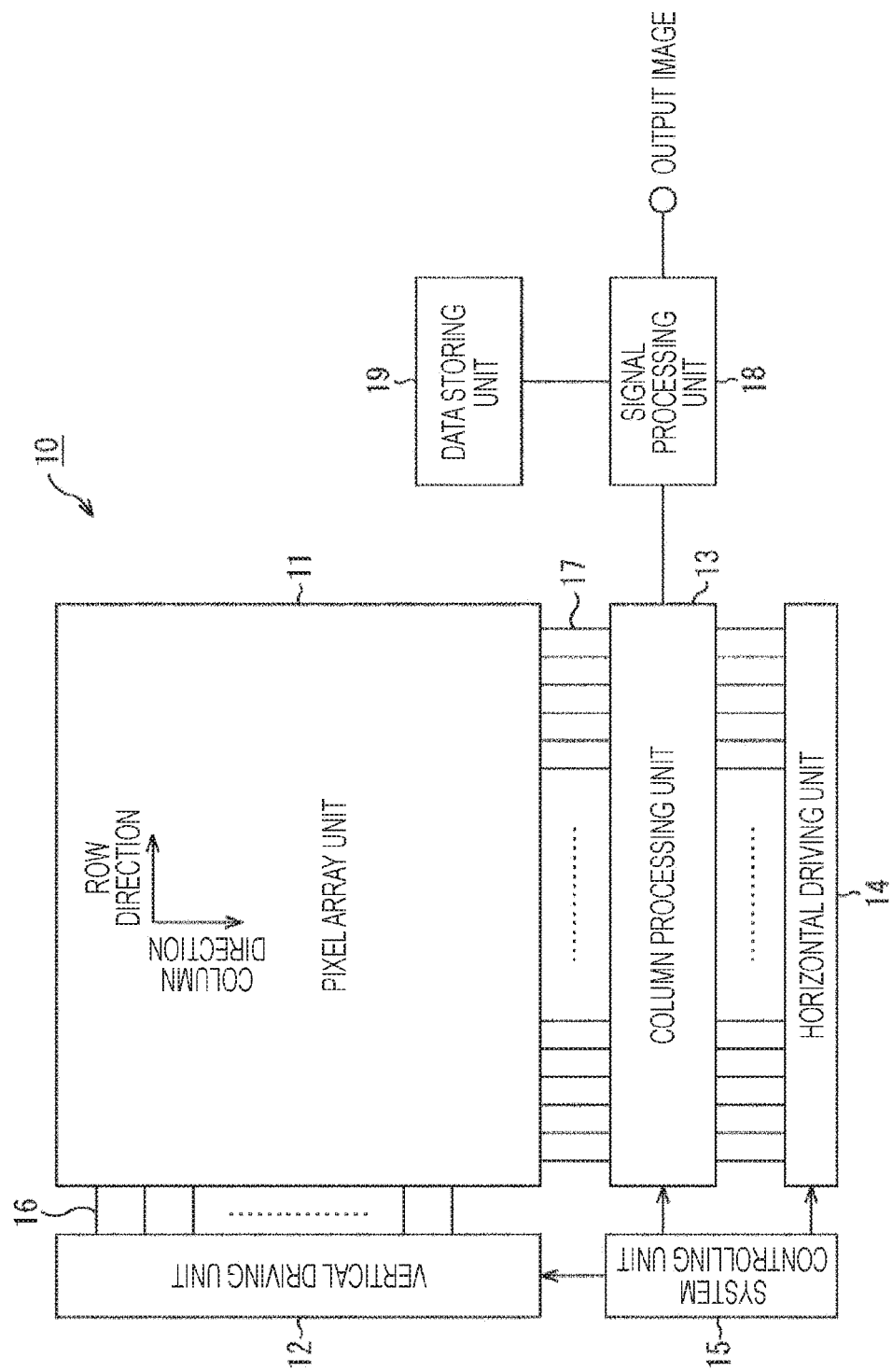
FIG. 1 is a system configuration diagram schematically illustrating a configuration of a CMOS image sensor to which the present technology is applied.

FIG. 1 is a system configuration diagram schematically illustrating a configuration of an imaging element to which the present technology is applied, for example, a CMOS image sensor which is a kind of an XY address type imaging element. Here, the CMOS image sensor is an image sensor manufactured by applying or partially using a CMOS process.

A CMOS image sensor 10 according to the present application example includes a pixel array unit 11 and a peripheral circuit unit. The peripheral circuit unit includes, for example, a vertical driving unit 12, a column processing unit 13, a horizontal driving unit 14, and a system controlling unit 15.

The CMOS image sensor 10 further includes a signal processing unit 18 and a data storing unit 19. The signal processing unit 18 and the data storing unit 19 may be mounted on a substrate where the CMOS image sensor 10 is amounted and may be arranged on a substrate that is different from a substrate on which the CMOS image sensor 10 is arranged. Furthermore, each processing of the signal processing unit 18 and the data storing unit 19 may be executed by an external signal processing unit that is provided on a substrate different from the substrate on which the CMOS image sensor 10 is provided, for example, a Digital Signal Processor (DSP) circuit and a software.

The pixel array unit 11 has a configuration in which a plurality of unit pixels (simply referred to as "pixel" below) is arranged in a row direction and a column direction. Here, the row direction indicates an arrangement direction of pixels in a pixel row (that is, horizontal direction), and the column direction indicates an arrangement direction of pixels in a pixel column (that is, vertical direction). Note that the row direction and the horizontal direction are referred to as a lateral direction, and the column direction and the vertical direction are referred to as an up/down direction.

The unit pixel includes a photoelectric converter (for example, a photodiode) that generates and accumulates electric charges according to an amount of received light and a plurality of transistors (so-called MOS transistor). An exemplary configuration of the unit pixel will be described later with reference to FIG. 2.

Furthermore, in the pixel array unit 11, a pixel driving line 16 as a row signal line is arranged along the row direction for each pixel row, and a vertical signal line 17 as a column signal line is arranged along the column direction for each pixel column. The pixel driving line 16 transmits a drive signal to perform driving when a signal is read from the pixel. Although the single pixel driving line 16 is illustrated in FIG. 1, the number of pixel driving lines is not limited to one. One end of the pixel driving line 16 is connected to an output end of corresponding each row of the vertical driving unit 12.

The vertical driving unit 12 includes a shift register, an address decoder, and the like, and drives the pixels of the pixel array unit 11 at the same time or row by row or the like. That is, the vertical driving unit 12 forms a driving unit for controlling an operation of each pixel of the pixel array unit 11, together with the system controlling unit 15 for controlling the vertical driving unit 12. A specific configuration of the vertical driving unit 12 is not illustrated. However, the vertical driving unit 12 generally includes two scanning systems, i.e., a read scanning system and a sweeping scanning system.

The read scanning system sequentially selects and scans the unit pixels of the pixel array unit 11 row by row to read a signal from the unit pixel. The signal read from the unit pixel is an analog signal. The sweeping scanning system sweeps and scans the read row to be read and scanned by the read scanning system prior to the reading and scanning by an exposure time.

By performing the sweep scanning by the sweeping scanning system, unnecessary electric charges are swept out from the photoelectric converter of the unit pixel in the read row. Accordingly, the photoelectric converter is reset. Then, by sweeping out (reset) the unnecessary electric charges by the sweeping scanning system, a so-called electronic shutter operation is performed. Here, the electronic shutter operation is an operation for throwing out the electric charge of the photoelectric converter and for newly starting exposure (start to accumulate electric charges).

A signal read by the read operation by the read scanning system corresponds to an amount of light received after the read operation performed immediately before that or after the electronic shutter operation. Then, a period from a read timing of the read operation performed immediately before or a sweep-out timing of the electronic shutter operation to the read timing of the read operation at this time is an exposure time of the electric charge in the unit pixel.

The signal output from each unit pixel in the pixel row selectively scanned by the vertical driving unit 12 is input to the column processing unit 13 via each vertical signal line 17 for each pixel column. The column processing unit 13 performs predetermined signal processing on the signal output from each pixel in the selected row via the vertical signal line 17 for each pixel column of the pixel array unit 11 and temporarily holds the pixel signal to which the signal processing has been performed.

Specifically, the column processing unit 13 performs at least noise removal processing, for example, Correlated Double Sampling (CDS) processing and Double Data Sampling (DDS) processing as signal processing. For example, by the CDS processing, a fixed pattern noise specific for a pixel, such as a reset noise and variation in thresholds of an amplification transistor in the pixel is removed. In addition to the noise removal processing, it is possible to make the column processing unit 13 have, for example, an analog-digital (AD) conversion function and convert an analog pixel signal into a digital signal and output the signal.

The horizontal driving unit 14 includes a shift register, an address decoder, and the like, and sequentially selects a unit circuit corresponding to each pixel column of the column processing unit 13. By the selection and scan by the horizontal driving unit 14, pixel signals to which the signal processing has been performed by the column processing unit 13 for each unit circuit are sequentially output.

The system controlling unit 15 includes a timing generator and the like for generating various timing signals and drives and controls the vertical driving unit 12, the column processing unit 13, the horizontal driving unit 14, and the like on the basis of various timings generated by the timing generator.

The signal processing unit 18 has at least a calculation processing function and performs various signal processing such as calculation processing on the pixel signal output from the column processing unit 13. The data storing unit 19 temporarily stores data necessary for the signal processing by the signal processing unit 18.

[Exemplary Configuration of Pixel]

Next, an exemplary configuration of each pixel 51a provided in the pixel array unit 11 will be described with reference to FIGS. 2 to 6.

Figure 2:
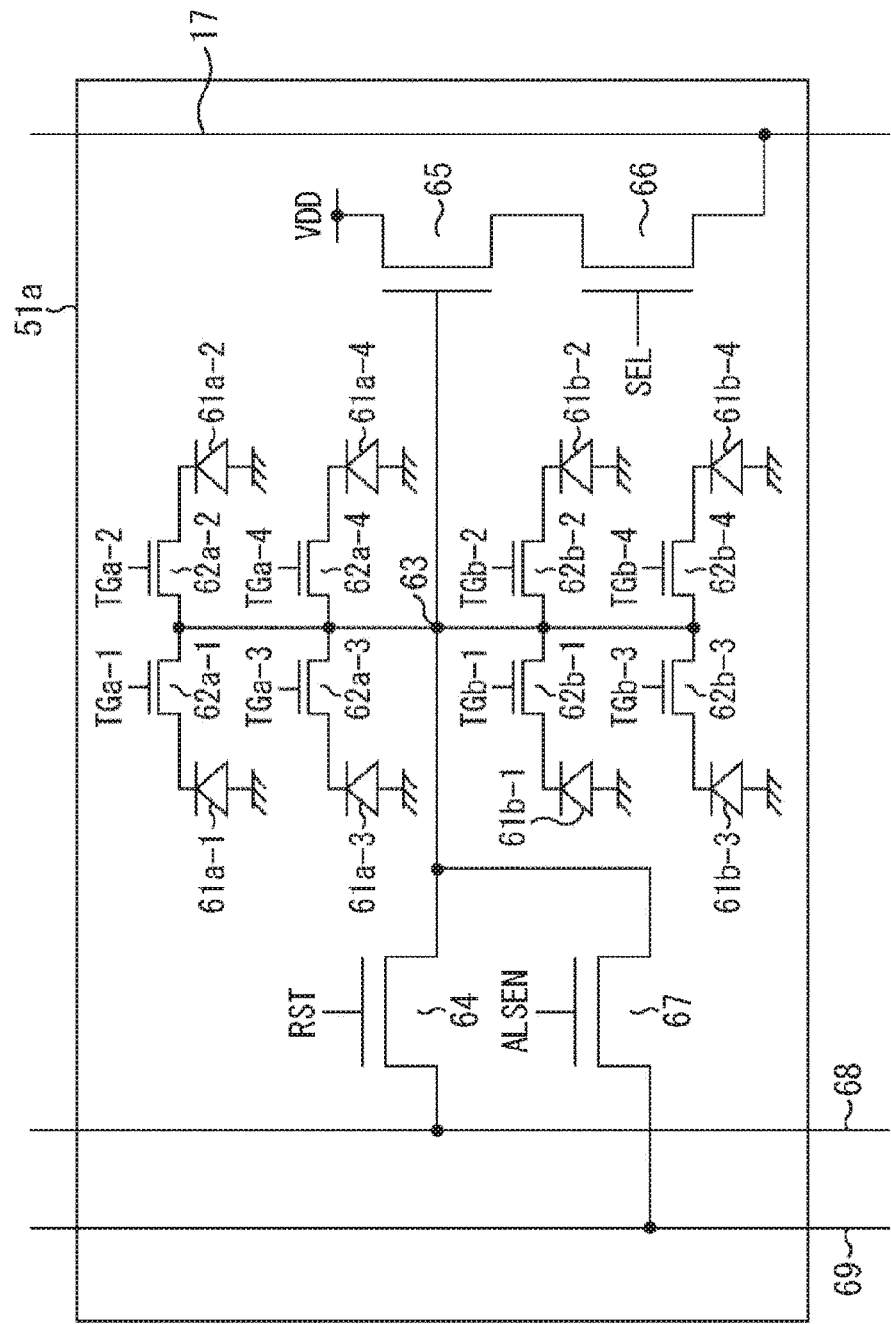
FIG. 2 is a circuit diagram of an exemplary configuration of a pixel.
Figure 3:
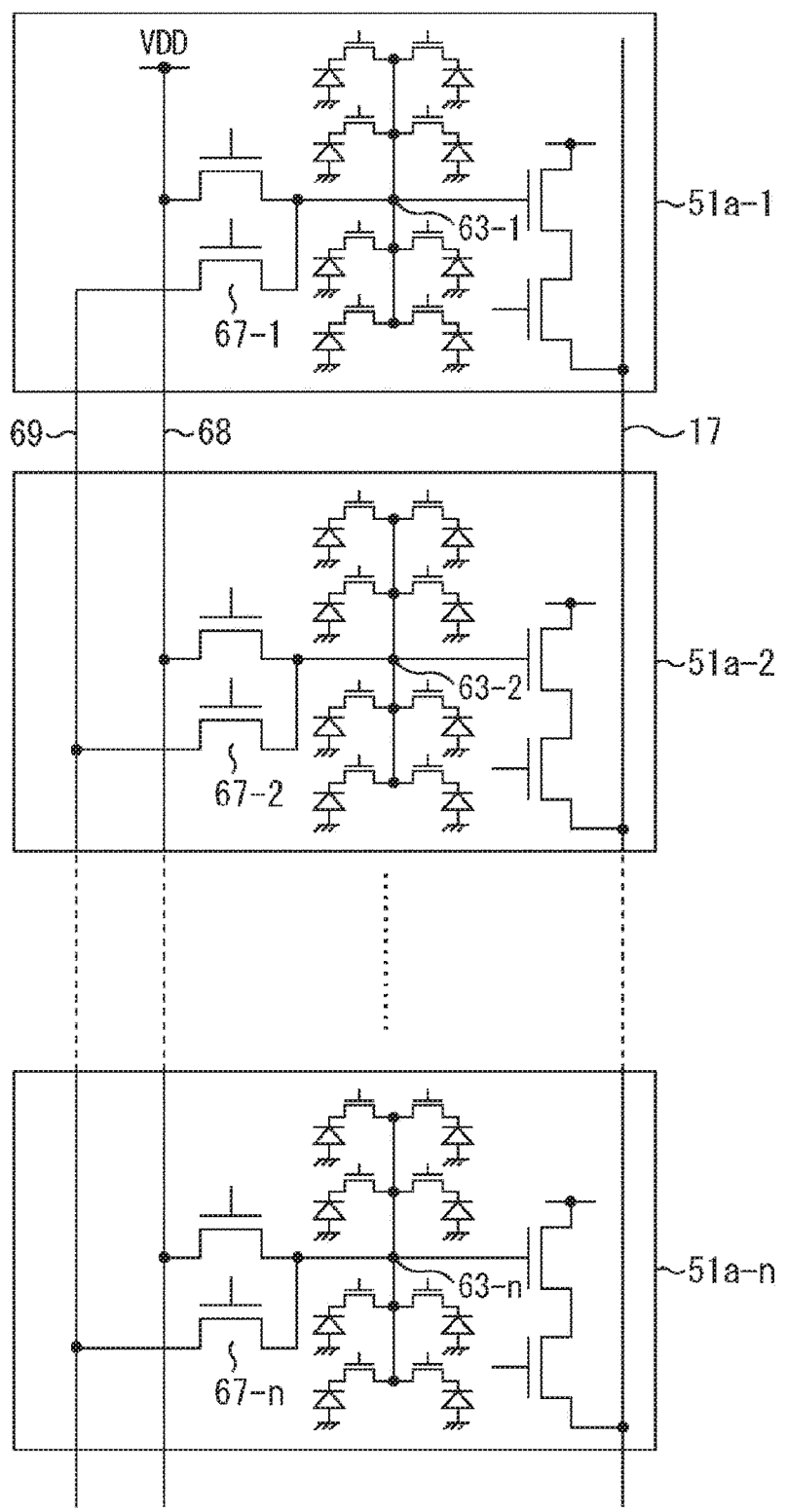
FIG. 3 is a circuit diagram of exemplary connection between the pixels.

First, an exemplary configuration of a circuit of the pixel 51a will be described with reference to FIGS. 2 and 3. FIG. 2 illustrates an exemplary configuration of the circuit of the single pixel 51a. FIG. 3 illustrates exemplary connection of the pixels 51a arranged in a column direction (vertical direction) of the pixel array unit 11.

The pixel 51a has a 2×4 shared pixel structure. Specifically, the pixel 51a includes 2×4 photoelectric conversion elements 61 including photoelectric conversion elements 61a-1 to 61a-4 and 61b-1 to 61b-4 and 2×4 transfer gate units 62 including transfer gate units 62a-1 to 62a-4 and 62b-1 to 62b-4. Then, the 2×4 photoelectric conversion elements 61 and the transfer gate units 62 share a charge voltage converting unit 63, a reset transistor 64, an amplification transistor 65, a selection transistor 66, and a coupling transistor 67.

Note that, hereinafter, the reset transistor 64, the amplification transistor 65, the selection transistor 66, and the coupling transistor 67 are collectively referred to as pixel transistors.

Each photoelectric conversion element 61 is, for example, a PN junction photodiode, receives light from a subject, generates electric charges corresponding to the amount of received light by photoelectric conversion, and accumulates the electric charges.

The transfer gate unit 62a-1 includes, for example, an N-channel MOS transistor and is provided between the photoelectric conversion element 61a-1 and the charge voltage converting unit 63. A drive signal TGa-1 is supplied to a gate electrode of the transfer gate unit 62a-1. The drive signal TGa-1 is a pulse signal that is active (on state) at a high level and is not active (off state) at a low level. Then, when the drive signal TGa-1 is activated and the transfer gate unit 62a-1 is turned on (becomes conductive), the electric charges accumulated in the photoelectric conversion element 61a-1 are transferred to the charge voltage converting unit 63 via the transfer gate unit 62a-1.

The transfer gate units 62a-2 to 62a-4 include, for example, N-channel MOS transistors and are respectively provided between the photoelectric conversion elements 61a-2 to 61a-4 and the charge voltage converting unit 63. Similarly to the transfer gate unit 62a-1, the transfer gate units 62a-2 to 62a-4 transfer the electric charges accumulated in the photoelectric conversion elements 61a-2 to 61a-4 to the charge voltage converting unit 63 in response to respective drive signals TGa-2 to TGa-4 supplied to the gate electrodes.

The transfer gate units 62b-1 to 62b-4 include, for example, N-channel MOS transistors and are respectively provided between the photoelectric conversion elements 61b-1 to 61b-4 and the charge voltage converting unit 63. Similarly to the transfer gate unit 62a-1, the transfer gate units 62b-1 to 62b-4 transfer the electric charges accumulated in the photoelectric conversion elements 61b-1 to 61b-4 to the charge voltage converting unit 63 in response to respective drive signals TGb-1 to TGb-4 supplied to the gate electrodes.

The charge voltage converting unit 63 is a floating diffusion region (FD) that converts the electric charge transferred from each photoelectric conversion element 61 into an electric signal, for example, a voltage signal and outputs the signal via each transfer gate unit 62. The charge voltage converting unit 63 is connected to the reset transistor 64 and the coupling transistor 67 and is connected to the vertical signal line 17 via the amplification transistor 65 and the selection transistor 66.

The reset transistor 64 is an element that appropriately initializes (reset) the charge voltage converting unit 63 and the like and, for example, includes an N-channel MOS transistor. A drain of the reset transistor 64 is connected to a power source of a power source voltage VDD via a power supply line 68, and a source is connected to the charge voltage converting unit 63. A drive signal RST is applied to a gate electrode of the reset transistor 64 as a reset signal. The drive signal RST is a pulse signal that is active (on state) at a high level and is not active (off state) at a low level. Then, when the drive signal RST is activated, the reset transistor 64 is turned on, and a potential of the charge voltage converting unit 63 and the like is reset to a level of the power source voltage VDD. That is, the charge voltage converting unit 63 and the like are initialized.

The amplification transistor 65 includes, for example, an N-channel MOS transistor. A gate electrode of the amplification transistor 65 is connected to the charge voltage converting unit 63, and a drain is connected to the power source of the power source voltage VDD. The amplification transistor 65 serves as an input unit of a source follower circuit that reads the electric charges obtained by photoelectric conversion by the photoelectric conversion element 61. That is, a source of the amplification transistor 65 is connected to the vertical signal line 17 via the selection transistor 66 so as to configure a source follower circuit together with a constant current source connected to one end of the vertical signal line 17.

The selection transistor 66 includes, for example, an N-channel MOS transistor and is connected between the source of the amplification transistor 65 and the vertical signal line 17. A drive signal SEL is supplied to a gate electrode of the selection transistor 66 as a selection signal. The drive signal SEL is a pulse signal that is active (on state) at a high level and is not active (off state) at a low level. Then, when the drive signal SEL is activated, the selection transistor 66 is turned on, and the pixel 51a in which the selection transistor 66 is provided is selected. When the pixel 51a is selected, a signal output from the amplification transistor 65 is read by the column processing unit 13 via the vertical signal line 17.

The coupling transistor 67 is a switch to connect the charge voltage converting unit 63 to the charge voltage converting unit 63 of the other pixel 51a that is arranged in the vertical direction with the charge voltage converting unit 63, and includes, for example, an N-channel MOS transistor. A drain of the coupling transistor 67 is connected to the charge voltage converting unit 63, and a source is connected to a capacitance coupling line 69. A drive signal ALSEN is applied to a gate electrode of the coupling transistor 67 as a coupling signal. The drive signal ALSEN is a pulse signal that is active (on state) at a high level and is not active (off state) at a low level. Then, when the drive signal ALSEN is activated, the coupling transistor 67 is turned on, and the charge voltage converting unit 63 is connected to the capacitance coupling line 69 via the coupling transistor 67. Then, the charge voltage converting unit 63 is connected to a charge voltage converting unit 63 of a pixel 51a of which a coupling transistor 67 is turned on of the other pixels 51a arranged in the same column along the vertical direction via the capacitance coupling line 69.

For example, in the example in FIG. 3, the charge voltage converting units 63a-1 to 63a-n of the respective pixels 51a-1 to 51a-n arranged in the vertical direction are connected in parallel to the capacitance coupling line 69 via the respective coupling transistors 67-1 to 67-n. The capacitance coupling line 69 is a signal line extending in a column direction (vertical direction) of the pixel array unit 11. Since ON/OFF of the coupling transistors 67-1 to 67-n can be individually controlled, it is possible to individually connect/separate the charge voltage converting units 63-1 to 63-n of the pixels 51a-1 to 51a-n to/from the capacitance coupling line 69. Therefore, a combination of the charge voltage converting units 63-1 to 63-n to be shared can be optionally selected, and the charge voltage converting units 63 can be flexibly shared between the pixels 51a. For example, in a case where a problem in characteristics such as a white point and a dark current occurs in one pixel 51a, it is possible to separate only the charge voltage converting unit 63 of the pixel 51a, and an optional combination of the other pixels 51a can share the charge voltage converting units 63.

In this way, the plurality of pixels 51a shares the charge voltage converting units 63. Then, for example, by controlling the number of charge voltage converting units 63 to be shared, a charge voltage conversion efficiency can be adjusted according to an amount of received light, and it is possible to increase a dynamic range and the like.

Furthermore, in each pixel 51a, a plurality of driving lines is wired, for example, for each pixel row as the pixel driving line 16 in FIG. 1. Then, the drive signals TGa-1 to TGb-4, RST, SEL, and ALSEN are supplied from the vertical driving unit 12 into the pixels via the plurality of driving lines as the pixel driving line 16.

Figure 4:
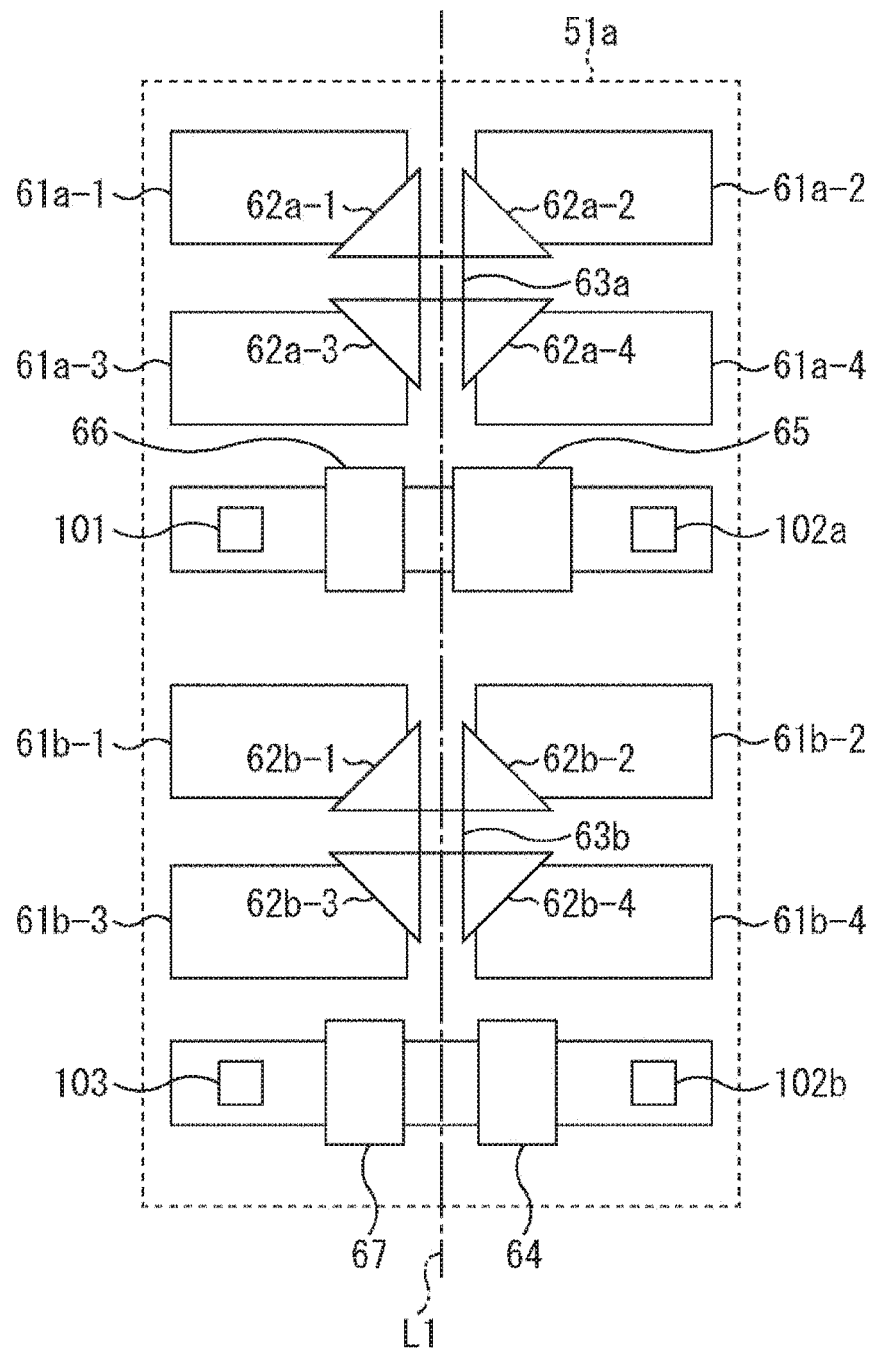
FIG. 4 is a schematic diagram of a first example of a pixel layout.
Figure 5:
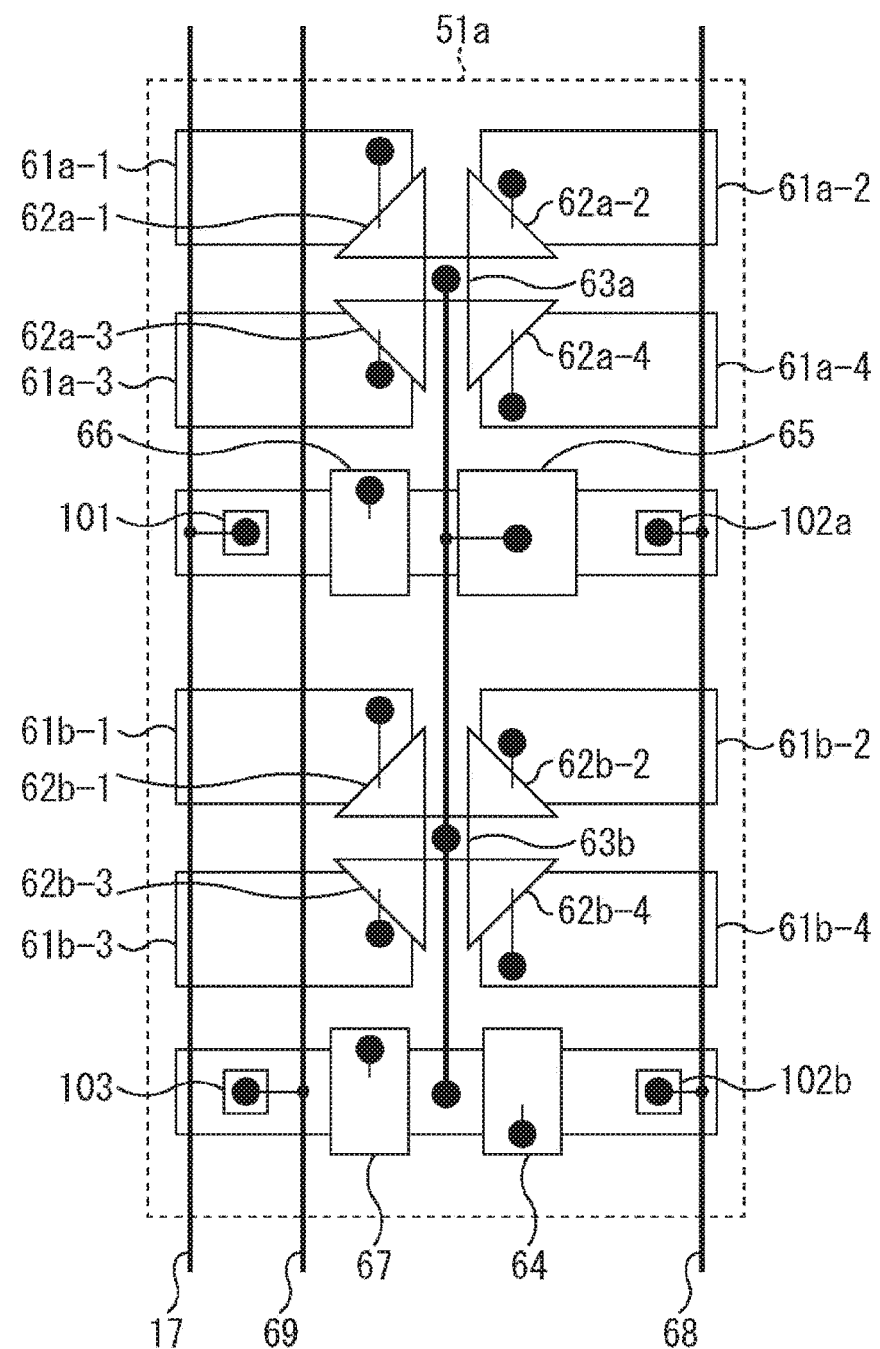
FIG. 5 is a schematic diagram of the first example of the pixel layout to which a first wiring layer is added.
Figure 6:
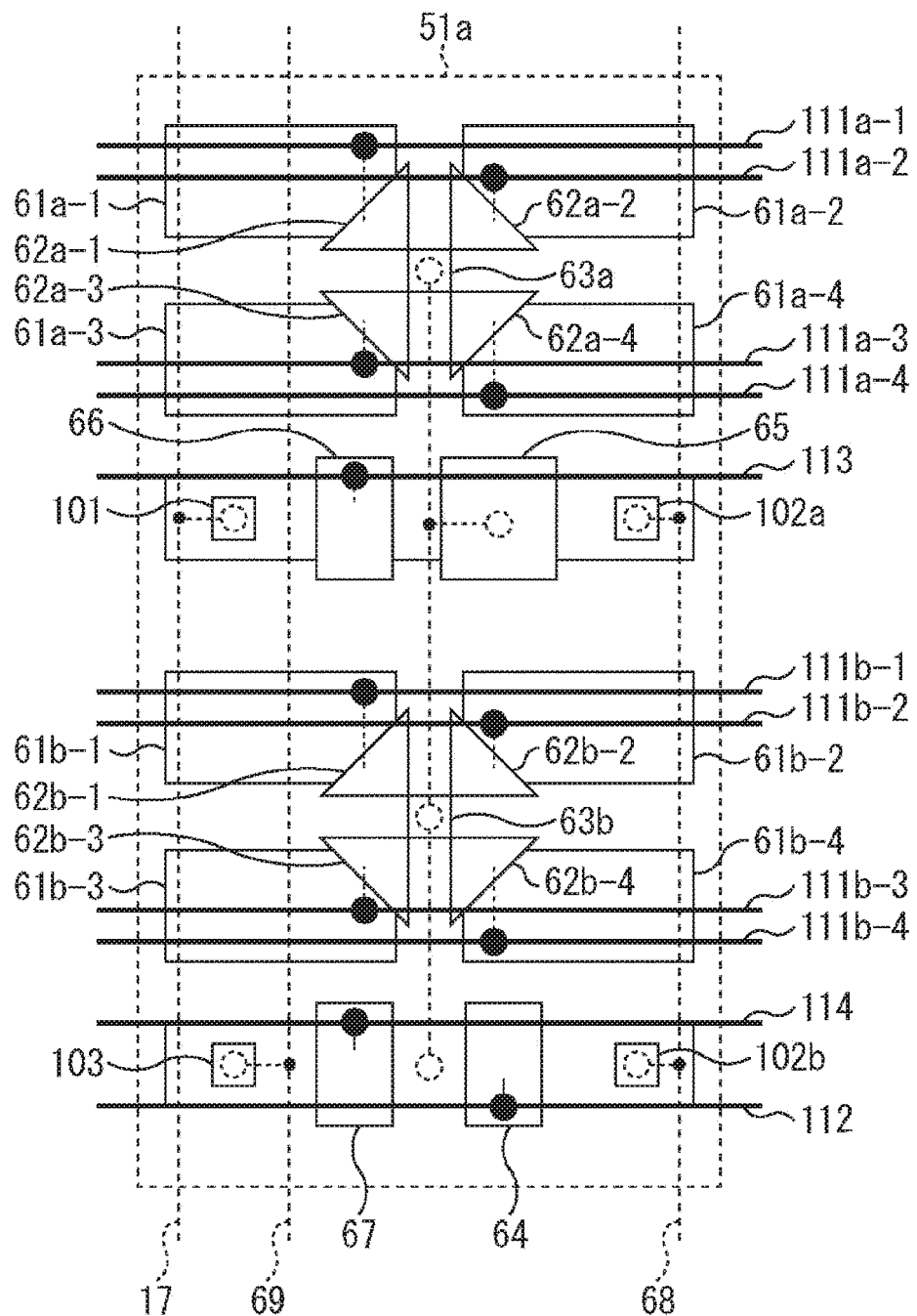
FIG. 6 is a schematic diagram of the first example of the pixel layout to which a second wiring layer is added.

Next, a layout of the pixel 51a will be described with reference to FIGS. 4 to 6. FIG. 4 is a diagram schematically illustrating a layout of a portion of the pixel 51a except for a wiring layer. Note that, in FIG. 4, an alternate long and short dash auxiliary line L1 is illustrated that passes through the substantially center of the pixel 51a in the horizontal direction and extends in the vertical direction. FIG. 5 is a diagram in which a first wiring layer is added to FIG. 4. FIG. 6 is a diagram in which a second wiring layer is added to FIG. 5. Note that, in FIG. 6, the first wiring layer is indicated by a dotted line to distinguish between the first wiring layer and the second wiring layer.

In this example, the charge voltage converting unit 63 in FIG. 2 is divided into two charge voltage converting units 63a and 63b, and the charge voltage converting units 63a and 63b are arranged adjacent to each other in the vertical direction at an interval on the auxiliary line L1. For example, the charge voltage converting unit 63a is connected to the transfer gate units 62a-1 to 62a-4, and the charge voltage converting unit 63b is connected to the transfer gate units 62b-1 to 62b-4.

Furthermore, the transfer gate units 62a-1 to 62a-4 surround the charge voltage converting unit 63a, and in addition, the photoelectric conversion elements 61a-1 to 61a-4 surround that. The transfer gate unit 62a-1 to 62a-4 and the photoelectric conversion elements 61a-1 to 61a-4 are symmetrically arranged about the charge voltage converting unit 63a in the vertical direction and the horizontal direction.

Specifically, the transfer gate unit 62a-1 is arranged on an upper left side of the charge voltage converting unit 63a in FIG. 4, and the photoelectric conversion element 61a-1 is arranged on an upper left side of the transfer gate unit 62a-1 in FIG. 4. The transfer gate unit 62a-2 is arranged on an upper right side of the charge voltage converting unit 63a in FIG. 4, and the photoelectric conversion element 61a-2 is arranged on an upper right side of the transfer gate unit 62a-2 in FIG. 4. The transfer gate unit 62a-3 is arranged on a lower left side of the charge voltage converting unit 63a in FIG. 4, and the photoelectric conversion element 61a-3 is arranged on a lower left side of the transfer gate unit 62a-3 in FIG. 4. The transfer gate unit 62a-4 is arranged on a lower right side of the charge voltage converting unit 63a in FIG. 4, and the photoelectric conversion element 61a-4 is arranged on a lower right side of the transfer gate unit 62a-4 in FIG. 4.

Furthermore, the transfer gate units 62b-1 to 62b-4 surround the charge voltage converting unit 63b, and in addition, the photoelectric conversion elements 61b-1 to 61b-4 surround that. The transfer gate unit 62b-1 to 62b-4 and the photoelectric conversion elements 61b-1 to 61b-4 are symmetrically arranged about the charge voltage converting unit 63b in the vertical direction and the horizontal direction.

Specifically, the transfer gate unit 62b-1 is arranged on an upper left side of the charge voltage converting unit 63b in FIG. 4, and the photoelectric conversion element 61b-1 is arranged on an upper left side of the transfer gate unit 62b-1 in FIG. 4. The transfer gate unit 62b-2 is arranged on an upper right side of the charge voltage converting unit 63b in FIG. 4, and the photoelectric conversion element 61b-2 is arranged on an upper right side of the transfer gate unit 62b-2 in FIG. 4. The transfer gate unit 62b-3 is arranged on a lower left side of the charge voltage converting unit 63b in FIG. 4, and the photoelectric conversion element 61b-3 is arranged on a lower left side of the transfer gate unit 62b-3 in FIG. 4. The transfer gate unit 62b-4 is arranged on a lower right side of the charge voltage converting unit 63b in FIG. 4, and the photoelectric conversion element 61b-4 is arranged on a lower right side of the transfer gate unit 62b-4 in FIG. 4.

A contact hole 101 for the vertical signal line 17, the selection transistor 66, the amplification transistor 65, and a contact hole 102a for the power supply line 68 are arranged in the horizontal direction from the left in order between the charge voltage converting units 63a and 63b. In addition, the contact holes 101 and 102a, the selection transistor 66 and the amplification transistor 65 are substantially symmetrically arranged with respect to the auxiliary line L1.

Below the charge voltage converting unit 63b, a contact hole 103 for the capacitance coupling line 69, the coupling transistor 67, the reset transistor 64, and a contact hole 102b for the power supply line 68 are arranged in order in the horizontal direction from the left. In addition, the contact holes 103 and 102b, and the coupling transistor 67 and the reset transistor 64 are substantially symmetrically arranged with respect to the auxiliary line L1.

Furthermore, as illustrated in FIG. 5, in the first wiring layer, a contact is embedded in the contact hole 101, and the vertical signal line 17 is connected to the contact. Contacts are respectively embedded in the contact holes 102a and 102b, and the power supply line 68 is connected to each contact. A contact is embedded in the contact hole 103, and the capacitance coupling line 69 is connected to the contact. The charge voltage converting units 63a and 63b are connected to each other and are connected to a diffusion layer between the reset transistor 64 and the coupling transistor 67.

Furthermore, as illustrated in FIG. 6, in the second wiring layer, driving lines 111a-1 to 111a-4 for the drive signals TGa-1 to TGa-4 are respectively connected to the transfer gate units 62a-1 to 62a-4. Driving lines 111b-1 to 111b-4 for the drive signals TGb-1 to TGb-4 are respectively connected to the transfer gate units 62b-1 to 62b-4. A driving line 112 for the drive signal RST is connected to the reset transistor 64. A driving line 113 for the drive signal SEL is connected to the selection transistor 66. A driving line 114 for the drive signal ALSEN is connected to the coupling transistor 67. These drive lines 111a-1 to 114 form the pixel driving line 16.

As described above, in the pixel 51a, the components are substantially symmetrically arranged about the auxiliary line L1. For example, by substantially symmetrically arranging the pixel transistors (reset transistor 64, amplification transistor 65, selection transistor 66, and coupling transistor 67), characteristics (for example, noise characteristics or the like) of each transistor are improved. Furthermore, by substantially symmetrically arranging the components other than the pixel transistors, in a state where the pixels 51a are arranged in the pixel array unit 11, for example, the layout such as wiring can be more freely formed.

Furthermore, for example, it is possible to arrange components in the horizontal row, in which the amplification transistor 65 and the selection transistor 66 are arranged, in a reverse order, and it is possible to arrange components in the horizontal direction, in which the reset transistor 64 and the coupling transistor 67 are arranged, in a reverse order.

2. Modification

A modification of the embodiment of the present technology will be described below.

[Modification Regarding Pixel Configuration]

The configuration of the pixel according to the present technology is not limited to the examples described with reference to FIGS. 2 to 6, and any configuration can be employed.

Here, the modification of the configuration of the pixel will be described with reference to FIGS. 7 to 9. Note that, in FIGS. 7 to 9, portions corresponding to those in FIGS. 2 to 6 are denoted with the same reference numerals. However, for some reference numerals, alphabetical notations included in the reference numerals in FIGS. 2 to 6 are omitted as necessary.

(First Modification of Pixel Configuration)

Figure 7:
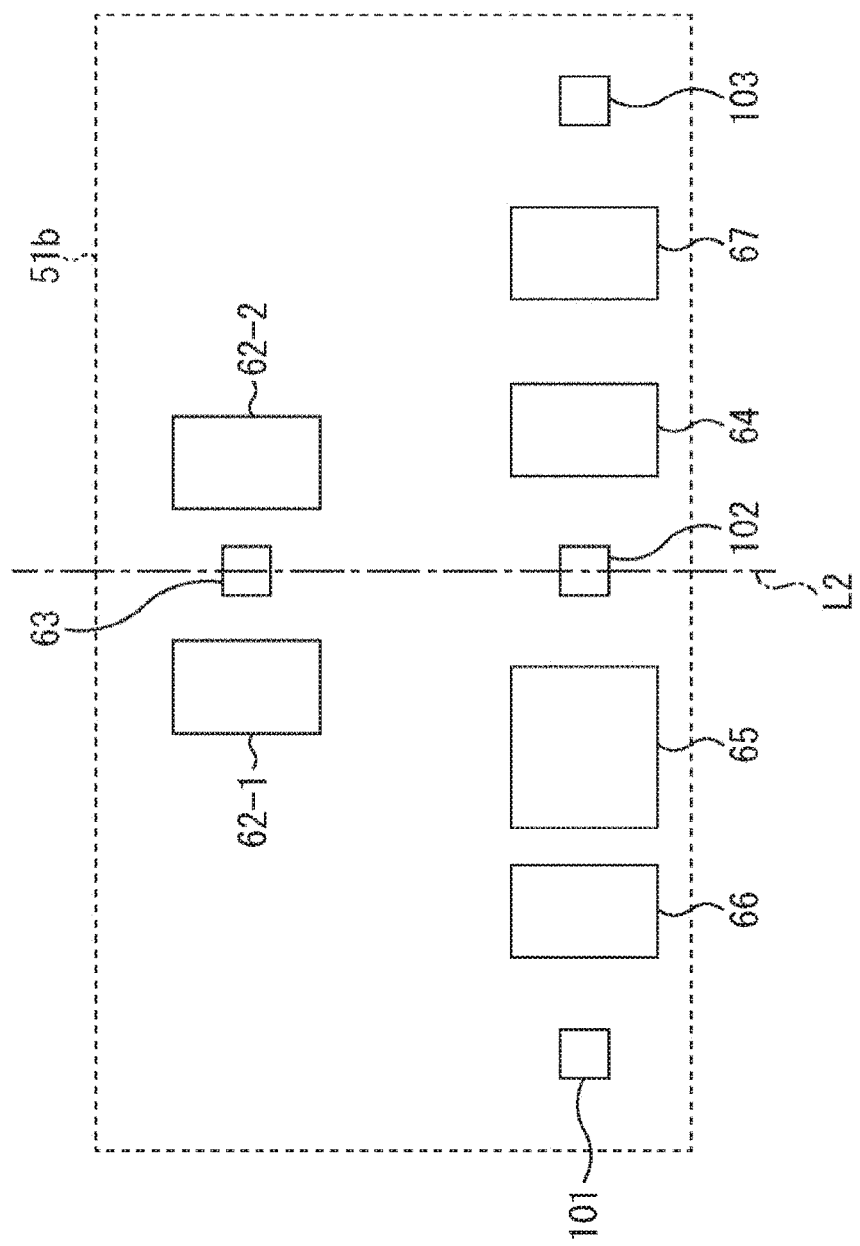
FIG. 7 is a schematic diagram of a second example of a pixel layout.

FIG. 7 schematically illustrates a layout of a pixel 51b which is a first modification. Note that, in FIG. 7, an alternate long and short dash auxiliary line L2 is illustrated that passes through the substantially center of the pixel 51b in the horizontal direction and extends in the vertical direction. Furthermore, in FIG. 7, a photoelectric conversion element 61 and a wiring layer are not illustrated.

The numbers of photoelectric conversion elements 61 and transfer gate units 62 and a layout of the components of the pixel 51b are different from those of the pixel 51a. Note that the configuration of the circuit is similar to the exemplary configuration of the circuit of the pixel 51a in FIG. 2 except that the numbers of photoelectric conversion elements 61 and transfer gate units 62 are different.

The pixel 51b has a 1×2 shared pixel structure. Specifically, the pixel 51b includes 1×2 photoelectric conversion elements 61 (not shown) including photoelectric conversion elements 61-1 and 61-2 and 1×2 transfer gate units 62 including transfer gate units 62-1 and 62-2. Then, the 1×2 photoelectric conversion elements 61 and transfer gate units 62 share a charge voltage converting unit 63, a reset transistor 64, an amplification transistor 65, a selection transistor 66, and a coupling transistor 67.

In the pixel 51b, the charge voltage converting unit 63 and a contact hole 102 are arranged adjacent to each other in the vertical direction at an interval on the auxiliary line L2.

On the left and right sides of the charge voltage converting unit 63, the transfer gate units 62-1 and 62-2 are symmetrically arranged about the auxiliary line L2.

On the left side of the contact hole 102, a contact hole 101, the selection transistor 66, and the amplification transistor 65 are arranged in the horizontal direction from the left in order. On the right side of the contact hole 102, the reset transistor 64, the coupling transistor 67, and a contact hole 103 are arranged in the horizontal direction from the left in order. The contact holes 101 and 103, the selection transistor 66 and the coupling transistor 67, and the amplification transistor 65 and the reset transistor 64 are substantially symmetrically arranged about the auxiliary line L2.

In this way, in the pixel 51b, similarly to the pixel 51a, the components are substantially symmetrically arranged about the auxiliary line L2, and an effect similar to the effect of the pixel 51a can be obtained.

Note that, for example, an order of the components in the row along the horizontal direction where the contact hole 102 is arranged may be reversed.

(Second Modification of Pixel Configuration)

Figure 8:
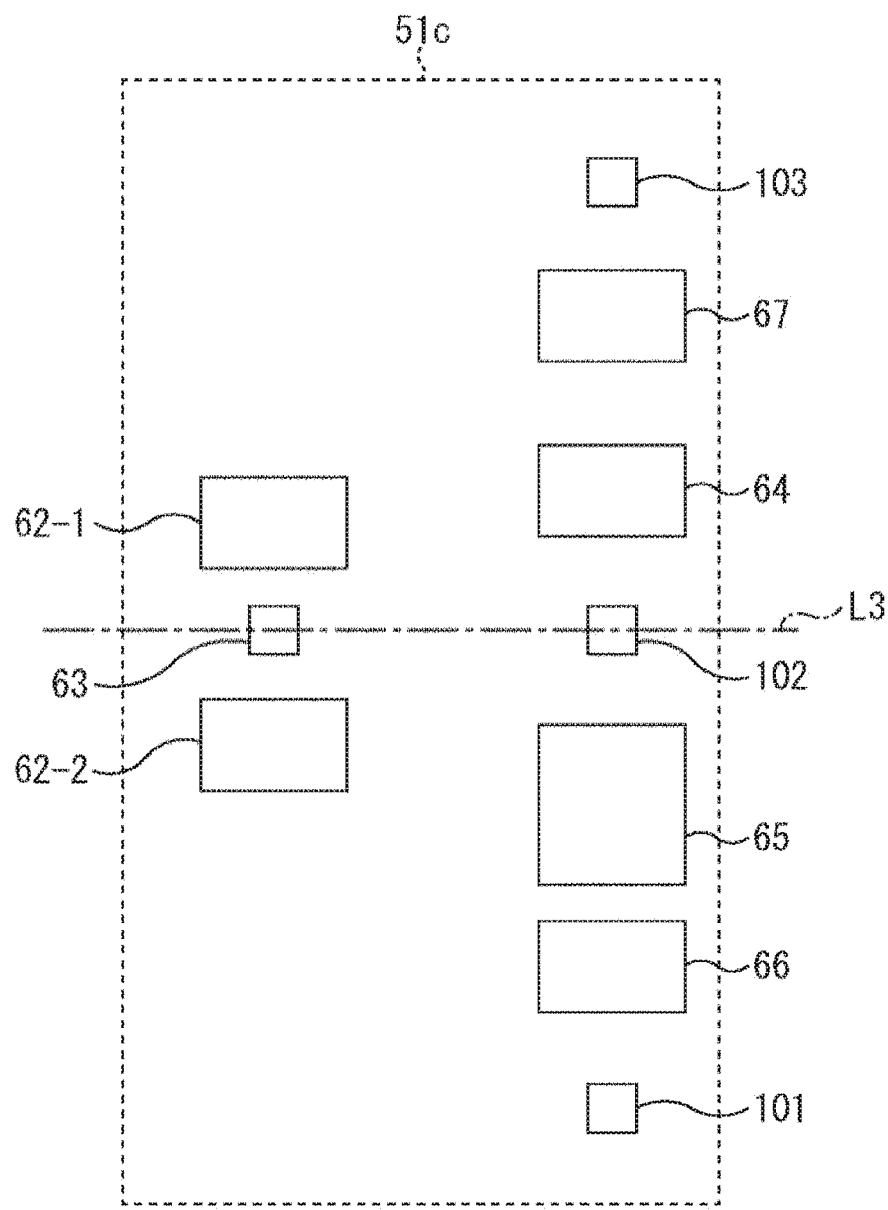
FIG. 8 is a schematic diagram of a third example of a pixel layout.

FIG. 8 schematically illustrates a layout of a pixel 51b which is a second modification. Note that, in FIG. 8, an alternate long and short dash auxiliary line L3 is illustrated that passes through the substantially center of the pixel 51c in the vertical direction and extends in the horizontal direction. Furthermore, in FIG. 7, a photoelectric conversion element 61 and a wiring layer are not illustrated.

A layout of the components of the pixel 51c is different from that of the pixel 51b in FIG. 7, and the circuit configurations are similar to each other.

In the pixel 51c, a charge voltage converting unit 63 and a contact hole 102 are arranged adjacent to each other in the horizontal direction at an interval on the auxiliary line L3.

On the upper and lower sides of the charge voltage converting unit 63, transfer gate units 62-1 and 62-2 are vertically symmetrically arranged about the auxiliary line L3.

On the upper side of the contact hole 102, a contact hole 103, a coupling transistor 67, and a reset transistor 64 are arranged in the vertical direction from the top in order. On the lower side of the contact hole 102, an amplification transistor 65, a selection transistor 66, and a contact hole 101 are arranged in the vertical direction from the top in order. The contact holes 103 and 101, the coupling transistor 67 and the selection transistor 66, and the reset transistor 64 and the amplification transistor 65 are substantially symmetrically arranged about the auxiliary line L3 in the vertical direction.

In this way, in the pixel 51c, the components are substantially symmetrically arranged about the auxiliary line L3 in the vertical direction. Then, even when the components are substantially symmetrically arranged in the vertical direction, an effect can be obtained that is similar to the effect in a case where the components are symmetrically arranged in the horizontal direction as in the pixels 51a and 51b.

Note that, for example, an order of the components in a column along the vertical direction where the contact hole 102 is arranged can be reversed.

Furthermore, for example, as described above, the components in the pixel may be substantially symmetrically arranged in two or more directions (for example, up/down direction and lateral direction) without substantially symmetrically arranging only in one direction.

(Third Modification of Pixel Configuration)

Figure 9:
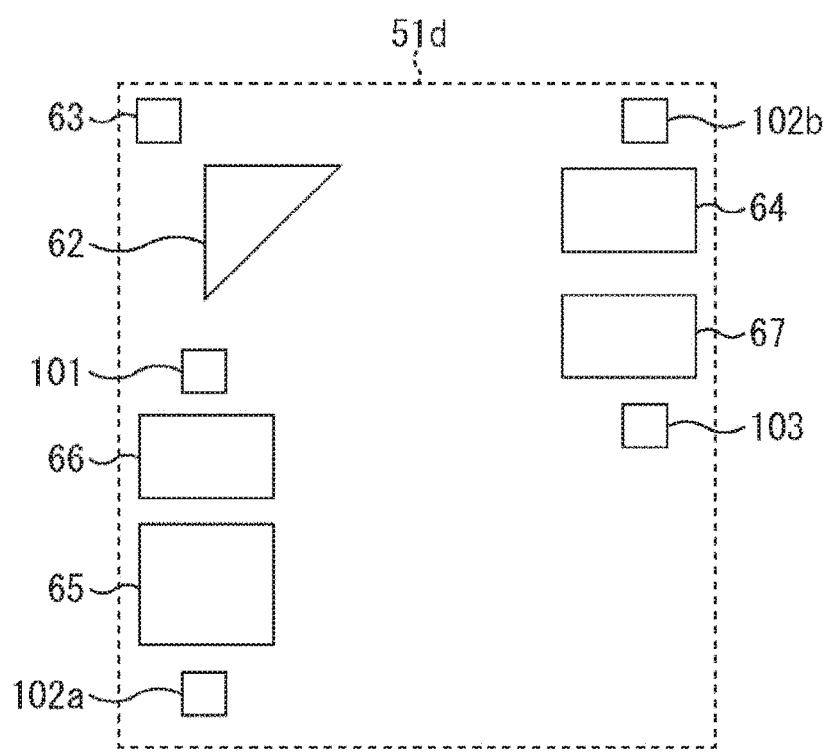
FIG. 9 is a schematic diagram of a fourth example of a pixel layout.

FIG. 9 schematically illustrates a layout of a pixel 51d which is a third modification. Note that, in FIG. 9, a photoelectric conversion element 61 and a wiring layer are not illustrated.

The numbers of photoelectric conversion elements 61 and transfer gate units 62 and a layout of component of the pixel 51d are different from those of the pixel 51a. Note that the configuration of the circuit is similar to the exemplary configuration of the circuit of the pixel 51a in FIG. 2 except that the numbers of photoelectric conversion elements 61 and transfer gate units 62 are different.

Unlike the other modifications, the pixel 51d does not have a shared pixel structure and has a single pixel structure. Specifically, in the pixel 51d, for a pair of the photoelectric conversion element 61 (not shown) and the transfer gate unit 62, a single charge voltage converting unit 63, reset transistor 64, amplification transistor 65, selection transistor 66, and coupling transistor 67 are provided.

In the pixel 51d, the charge voltage converting unit 63, the transfer gate unit 62, a contact hole 101, the selection transistor 66, the amplification transistor 65, and a contact hole 102a are arranged from the top in order in the vertical direction at the left end. In addition, a contact hole 102b, the reset transistor 64, the coupling transistor 67, and a contact hole 103 are arranged in the vertical direction from the top in order at the right end. A predetermined interval is provided between the column at the left end and the column at the right end. Furthermore, each of pairs of the charge voltage converting unit 63 and the contact hole 102b, the transfer gate unit 62 and the reset transistor 64, the contact hole 101 and the coupling transistor 67, and the selection transistor 66 and the contact hole 103 is arranged at the substantially same position in the vertical direction.

(Modification of Other Pixel Configuration)

Furthermore, the present technology can be applied, for example, to a case where a pixel having a configuration of supplying a selection signal from a vertical driving unit 12 to each pixel is used without providing a selection transistor 66 in the pixel. In this case, for example, in the example in FIG. 4, a bilaterally symmetrical layout of the pixel 51a is maintained by arranging an amplification transistor 65 on an auxiliary line L1.

Note that, in a case where the selection transistor 66 is not provided, to maintain the symmetrical layout of the pixel, a dummy transistor that is not actually used can be arranged.

Furthermore, in a case where the layout is restricted and it is difficult to symmetrically arrange all the components, pixel transistors may be preferentially arranged in a symmetrical way.

[Other Modifications]

Furthermore, in the above, an example has been described in which the charge voltage converting unit 63 is shared by the pixels arranged in the same column along the vertical direction. However, arrangement of the pixels sharing the charge voltage converting unit 63 may be optionally set.

For example, by dividing a capacitance coupling line 69 along the vertical direction into a plurality of pieces, the pixels in the same column may be divided into groups that respectively share the charge voltage converting units 63. Furthermore, for example, the pixels arranged in the horizontal direction may share the charge voltage converting unit 63 by extending the capacitance coupling line 69 in a row direction (horizontal direction) of a pixel array unit 11. In addition, for example, it is preferable that the charge voltage converting units 63 for the pixels in respective rectangular areas of m rows×n columns be connected to the capacitance coupling line 69 in parallel via the coupling transistor 67 and share the charge voltage converting unit 63.

Furthermore, the present technology can be applied to both of a surface irradiation type and a rear surface irradiation type CMOS image sensors.

Furthermore, in the present technology, an optional pixel driving method can be employed. For example, either driving method of a global shutter system or a rolling shutter system may be used.

Furthermore, the application of the present technology is not limited to the CMOS image sensor, and the present technology can be applied to an imaging element other than the CMOS image sensor.

3. Exemplary Usage of Imaging Element

Figure 10:
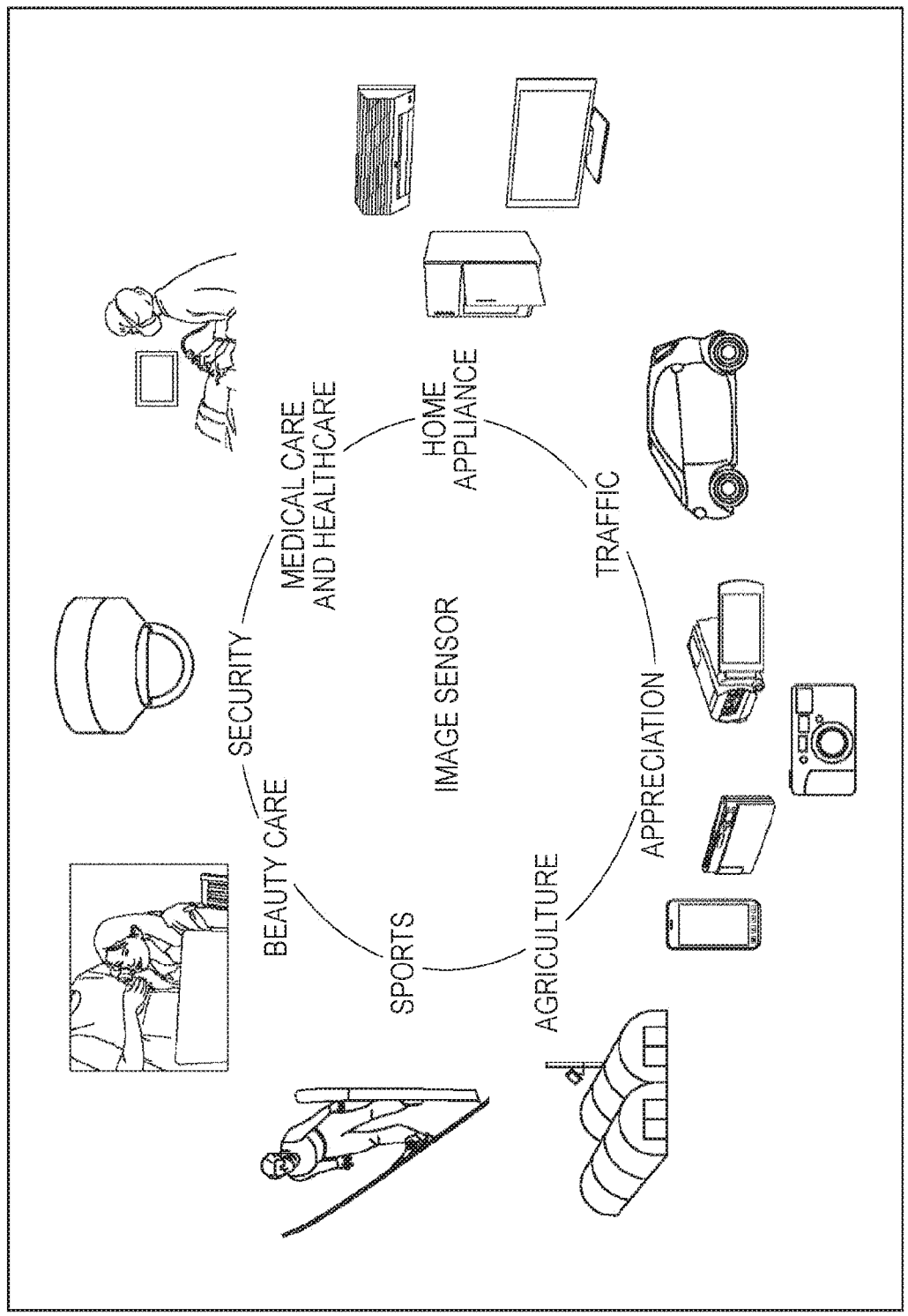
FIG. 10 is a diagram of an exemplary usage of an imaging element.

FIG. 10 is a diagram illustrating an exemplary usage of the imaging element.

The imaging element described above can be used, for example, in various cases in which light such as visible light, infrared light, ultraviolet light, and X-rays are sensed as follows.

- A device which images an image to be used for appreciation, such as a digital camera and a portable device with a camera function
- A device which is used for traffic, such as an in-vehicle sensor for imaging the front, rear, surroundings, inside, and the like of a car for safe driving such as automatic stop, recognition of a driver's state, and the like, a monitoring camera for monitoring a traveling vehicle and a road, a distance measuring sensor for measuring a distance between vehicles, and the like
- A device which is used for home appliances, such as a TV, a refrigerator, an air conditioner, and the like to image a gesture of a user and operates the device according to the gesture
- A device which used for medical care and healthcare, such as an endoscope, a device for angiography by receiving infrared light, and the like
- A device which is used for security, such as a security monitoring camera, a camera for person authentication, and the like
- A device which is used for beauty care, such as a skin measuring instrument for photographing skin, a microscope for photographing a scalp, and the like A device which is used for sports, such as an action camera and a wearable camera for sports and the like A device which is used for agriculture, such as a camera for monitoring conditions of fields and crops

[Imaging Device]

Figure 11:
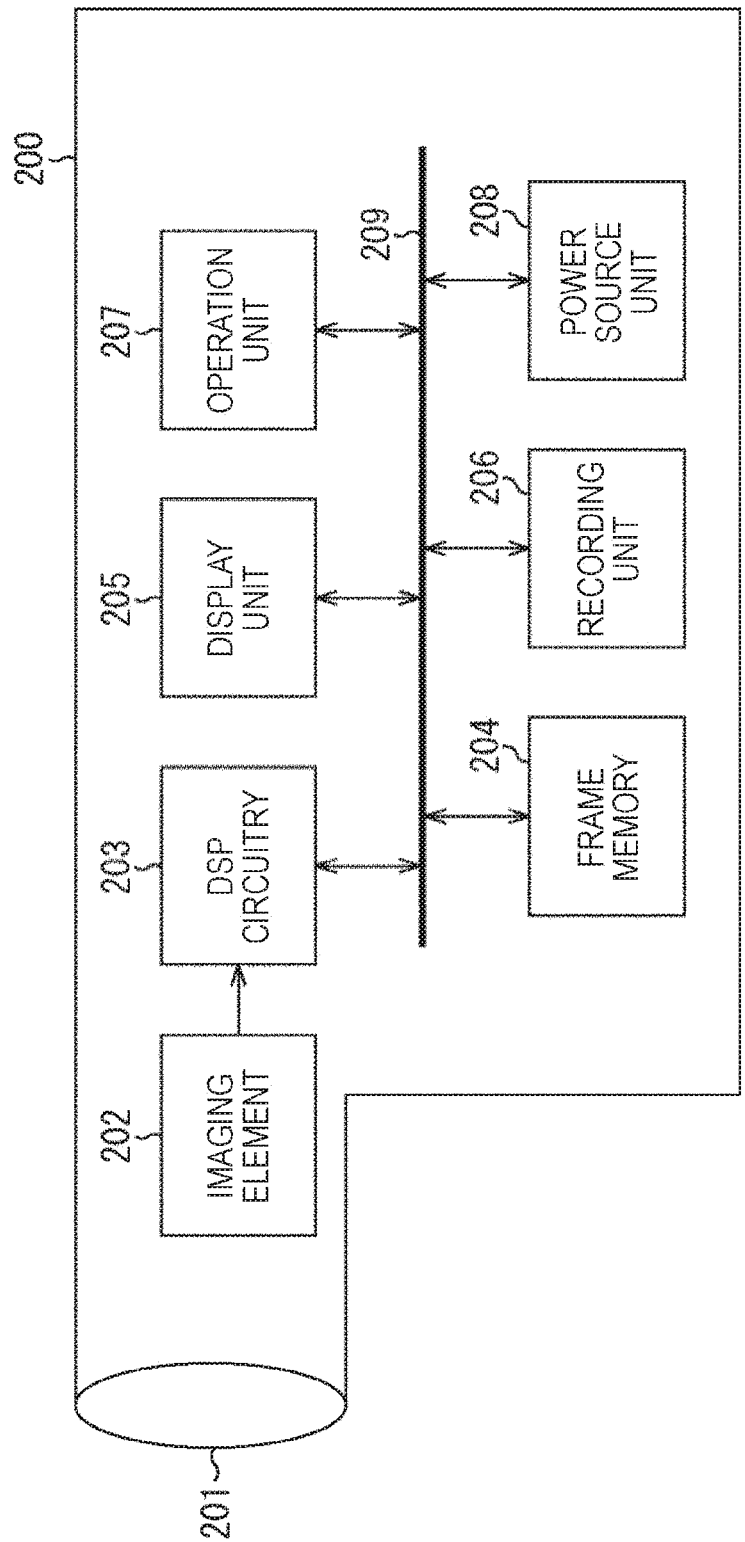
FIG. 11 is a block diagram of an exemplary configuration of an electronic device.

FIG. 11 is a diagram illustrating an exemplary configuration of an electronic device 200 having an imaging element to which the present technology is applied.

The electronic device 200 is, for example, an imaging device such as a digital still camera and a video camera, a mobile terminal device such as a smartphone and a tablet type terminal, and the like.

In FIG. 11, the electronic device 200 includes a lens 201, an imaging element 202, a DSP circuit 203, a frame memory 204, a display unit 205, a recording unit 206, an operation unit 207, and a power source unit 208. Furthermore, in the electronic device 200, the DSP circuit 203, the frame memory 204, the display unit 205, the recording unit 206, the operation unit 207, and the power source unit 208 are connected to each other via a bus line 209.

For example, the imaging element 202 corresponds to the CMOS image sensor 10.

The DSP circuit 203 is a camera signal processing circuit for processing a signal supplied from the imaging element 202. The DSP circuit 203 outputs image data obtained by processing the signal from the imaging element 202. The frame memory 204 temporarily holds the image data processed by the DSP circuit 203 in frame units.

The display unit 205 includes, for example, a panel type display device such as a liquid crystal panel and an organic Electro Luminescence (EL) panel and displays a moving image or a still image imaged by the imaging element 202. The recording unit 206 records the image data of the moving image or the still image imaged by the imaging element 202 to a recording medium such as a semiconductor memory or a hard disk.

The operation unit 207 outputs an operation instruction regarding various functions of the electronic device 200 according to a user's operation. The power source unit 208 appropriately supplies various power sources to be an operation power source of the DSP circuit 203, the frame memory 204, the display unit 205, the recording unit 206, and the operation unit 207 to these components which are supply targets.

[Application to In-Vivo Information Acquiring System]

Furthermore, for example, a technology according to the present disclosure (present technology) may be applied to an endoscopic surgery system.

Figure 12:
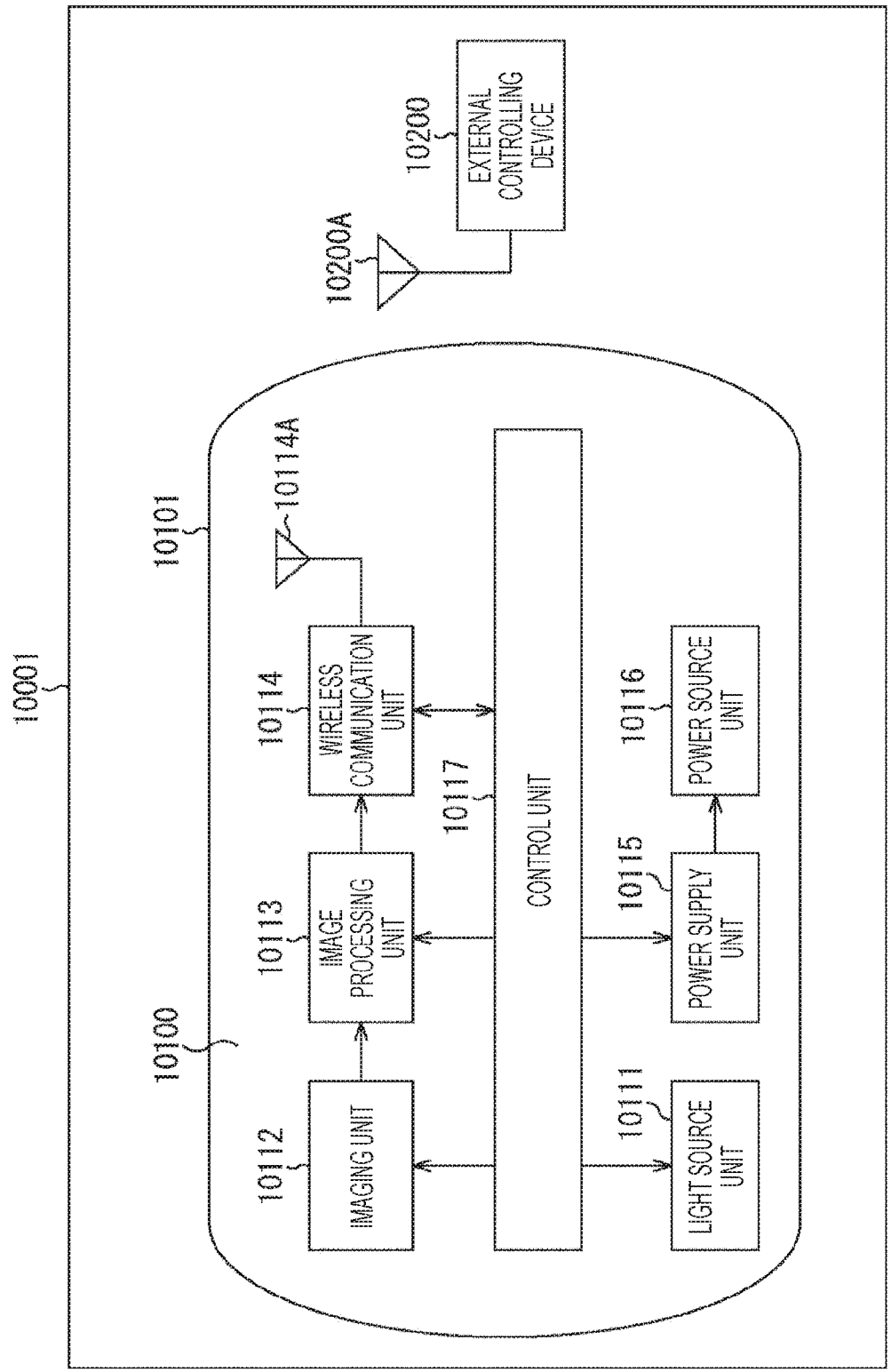
FIG. 12 is a block diagram of an exemplary schematic configuration of an in-vivo information acquiring system.

FIG. 12 is a block diagram illustrating an exemplary schematic configuration of a patient in-vivo information acquiring system using a capsulated endoscope to which the technology according to the present disclosure (present technology) may be applied.

An in-vivo information acquiring system 10001 includes a capsulated endoscope 10100 and an external controlling device 10200.

The capsulated endoscope 10100 is swallowed by a patient at the time of examination. The capsulated endoscope 10100 has an imaging function and a wireless communication function. While moving through internal organs such as a stomach and intestines by peristaltic movement or the like until being naturally discharged from the patient, the capsulated endoscope 10100 sequentially images the images of the inside of the organs (referred to as in-vino image below) at predetermined intervals and sequentially wirelessly transmits information regarding the in-vino image to the external controlling device 10200 outside the body.

The external controlling device 10200 integrally controls an operation of the in-vivo information acquiring system 10001. Furthermore, the external controlling device 10200 receives the information regarding the in-vino image transmitted from the capsulated endoscope 10100 and generates image data to display the in-vino image on a display device (not shown) on the basis of the received information regarding the in-vino image.

In this way, the in-vivo information acquiring system 10001 can obtain an in-vino image of a state in the body of the patient as needed from the time when the capsulated endoscope 10100 is swallowed to the time when the capsulated endoscope 10100 is discharged.

The configurations and functions of the capsulated endoscope 10100 and the external controlling device 10200 will be described in more detail.

The capsulated endoscope 10100 has a capsule-shaped casing 10101, and in the casing 10101, a light source unit 10111, an imaging unit 10112, an image processing unit 10113, a wireless communication unit 10114, a power supply unit 10115, a power source unit 10116, and a control unit 10117 are housed.

The light source unit 10111 includes, for example, a light source such as a Light Emitting Diode (LED) and irradiates an imaging field of view of the imaging unit 10112 with light.

The imaging unit 10112 includes an imaging element and an optical system including a plurality of lenses provided in front of the imaging element. Reflected light (referred to as observation light below) of the light emitted to a body tissue to be observed is collected by the optical system and enters the imaging element. In the imaging unit 10112, the imaging element photoelectrically converts the entered observation light and generates an image signal corresponding to the observation light. The image signal generated by the imaging unit 10112 is provided to the image processing unit 10113.

The image processing unit 10113 includes a processor such as a Central Processing Unit (CPU) and a Graphics Processing Unit (GPU) and performs various signal processing on the image signal generated by the imaging unit 10112. The image processing unit 10113 provides the signal-processed image signal to the wireless communication unit 10114 as RAW data.

The wireless communication unit 10114 performs predetermined processing such as modulation processing on the image signal on which the signal processing has been performed by the image processing unit 10113 and transmits the image signal to the external controlling device 10200 via an antenna 10114A. Furthermore, the wireless communication unit 10114 receives a control signal regarding drive and control of the capsulated endoscope 10100 from the external controlling device 10200 via the antenna 10114A. The wireless communication unit 10114 provides the control signal received from the external controlling device 10200 to the control unit 10117.

The power supply unit 10115 includes an antenna coil for receiving power, a power regeneration circuit that regenerates power from a current generated by the antenna coil, a booster circuit, and the like. The power supply unit 10115 generates power by using a so-called contactless charging principle.

The power source unit 10116 includes a secondary battery and stores the power generated by the power supply unit 10115. In FIG. 12, to avoid complication of the drawing, arrow and the like indicating a supply destination of the power from the power source unit 10116 is not illustrated.

However, the power stored in the power source unit 10116 is supplied to the light source unit 10111, the imaging unit 10112, the image processing unit 10113, the wireless communication unit 10114, and the control unit 10117 and may be used to drive these units.

The control unit 10117 includes a processor such as a CPU and appropriately controls drive of the light source unit 10111, the imaging unit 10112, the image processing unit 10113, the wireless communication unit 10114, and the power supply unit 10115 in response to the control signal transmitted from the external controlling device 10200.

The external controlling device 10200 includes a processor such as a CPU and a GPU, a microcomputer or a control board on which storage elements such as a processor, a memory, and the like are provided together. The external controlling device 10200 transmits the control signal to the control unit 10117 of the capsulated endoscope 10100 via the antenna 10200A to control an operation of the capsulated endoscope 10100. In the capsulated endoscope 10100, for example, a condition of light irradiation with respect to an object to be observed of the light source unit 10111 may be changed according to the control signal from the external controlling device 10200. Furthermore, an imaging condition (for example, frame rate, exposure value, and the like of imaging unit 10112) may be changed according to the control signal from the external controlling device 10200. Furthermore, according to the control signal from the external controlling device 10200, a content of processing by the image processing unit 10113 and a condition regarding transmission of the image signal from the wireless communication unit 10114 (for example, transmission interval, the number of images to be transmitted, and the like) may be changed.

In addition, the external controlling device 10200 performs various image processing on the image signal transmitted from the capsulated endoscope 10100 and generates image data to display the imaged in-vino image on a display device. As the image processing, various signal processing can be performed, for example, development processing (demosaic processing), image quality enhancement processing (band emphasis processing, super-resolution processing, Noise Reduction (NR) processing, and/or camera shake correction processing), and/or enlargement processing (electronic zoom processing). The external controlling device 10200 controls the drive of the display device and displays the imaged in-vino image on the basis of the generated image data. Alternatively, the external controlling device 10200 may make a recording device (not shown) record the generated data or make a printing device (not shown) print and output the generated image data.

An example of the in-vivo information acquiring system to which the technology according to the present disclosure can be applied has been described above. The technology according to the present disclosure can be applied to the imaging unit 10112 in the above configuration. Specifically, the CMOS image sensor 10 in FIG. 1 can be applied to the imaging unit 10112. By applying the technology according to the present disclosure to the imaging unit 10112, for example, an image of a surgical site with less noise and a wide dynamic range can be obtained. Therefore, examination can be more accurately performed.

[Application to Endoscopic Surgery System]

In addition, for example, a technology according to the present disclosure (present technology) may be applied to an endoscopic surgery system.

Figure 13:
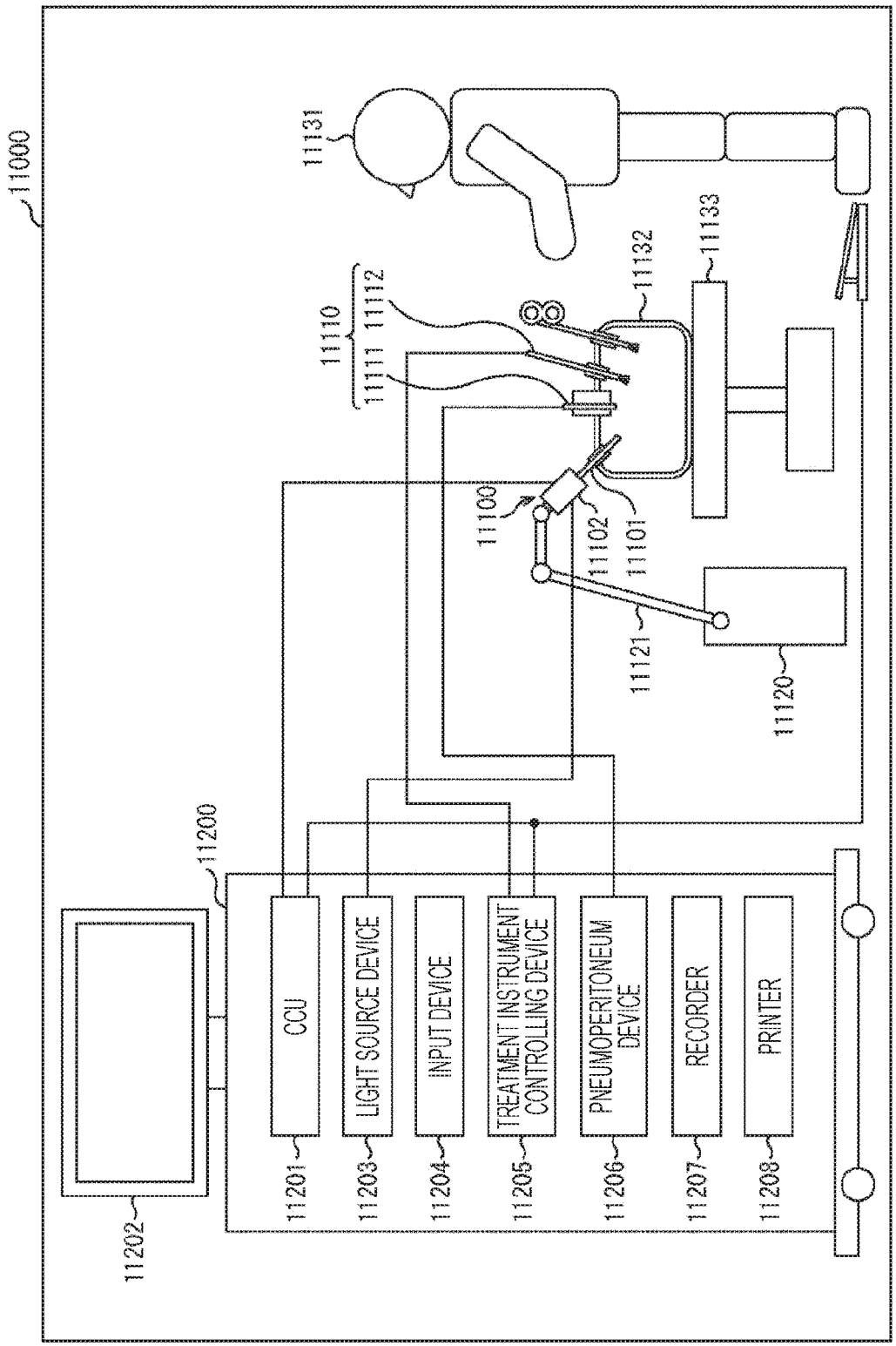
FIG. 13 is a diagram of an exemplary schematic configuration of an endoscopic surgery system.

FIG. 13 is a diagram of an exemplary schematic configuration of an endoscopic surgery system to which the technology according to the present disclosure (present technology) may be applied.

In FIG. 13, a state is illustrated in which an operator (doctor) 11131 is operating a patient 11132 on a patient bed 11133 by using an endoscopic surgery system 11000. As illustrated in FIG. 13, the endoscopic surgery system 11000 includes an endoscope 11100, other surgical tools 11110 such as a pneumoperitoneum tube 11111 and an energy treatment instrument 11112, a supporting arm device 11120 for supporting the endoscope 11100, and a cart 11200 on which various devices for endoscopic surgery are mounted.

The endoscope 11100 includes a lens barrel 11101 of which a portion with a predetermined length from a top end is inserted into a body cavity of the patient 11132 and a camera head 11102 connected to a base end of the lens barrel 11101. In the illustrated example, the endoscope 11100 formed as a so-called rigid endoscope having a rigid lens barrel 11101 is illustrated. However, the endoscope 11100 may be formed as a so-called flexible endoscope having a flexible lens barrel.

At the front end of the lens barrel 11101, an opening in which an objective lens is fitted is provided. A light source device 11203 is connected to the endoscope 11100, and light generated by the light source device 11203 is guided to the front end of the lens barrel by a light guide extending in the lens barrel 11101 and is irradiated to the object to be observed in the body cavity of the patient 11132 through the objective lens. Note that the endoscope 11100 may be a direct-view endoscope, an oblique-view endoscope, or a side-view endoscope.

An optical system and an imaging element are provided in the camera head 11102, and light reflected by the object to be observed (observation light) is collected by the optical system to the imaging element. The imaging element photoelectrically converts the observation light and generates an electric signal corresponding to the observation light, that is, an image signal corresponding to an observation image. The image signal is transmitted to a Camera Control Unit (CCU) 11201 as RAW data.

The CCU 11201 includes a Central Processing Unit (CPU), a Graphics Processing Unit (GPU), and the like and integrally controls operations of the endoscope 11100 and the display device 11202. In addition, the CCU 11201 receives the image signal from the camera head 11102 and performs various image processing on the image signal to display an image based on the image signal, for example, development processing (demosaic processing), or the like.

The display device 11202 displays the image based on the image signal to which the image processing has been performed by the CCU 11201 under the control by the CCU 11201.

The light source device 11203 includes a light source such as a Light Emitting Diode (LED), for example, and supplies irradiation light, at the time when a surgical site or the like is imaged, to the endoscope 11100.

An input device 11204 is an input interface relative to the endoscopic surgery system 11000. A user can input various information and input instructions to the endoscopic surgery system 11000 via the input device 11204. For example, the user inputs an instruction or the like to change an imaging condition (kind, magnification, focal length, and the like of irradiation light) of the endoscope 11100.

A treatment instrument controlling device 11205 controls drive of an energy treatment instrument 11112 for cauterizing or cutting tissue or sealing a blood vessel. To secure a field of view and an operation space of an operator by the endoscope 11100, a pneumoperitoneum device 11206 injects gas into the body cavity through a pneumoperitoneum tube 11111 to swell the body cavity of the patient 11132. A recorder 11207 is a device capable of recording various information regarding surgery. A printer 11208 is a device capable of printing various information regarding surgery in various formats such as a text, an image, a graph, and the like.

It should be noted that the light source device 11203 that supplies the irradiation light at the time of imaging the surgical site to the endoscope 11100 can include a white light source including, for example, a LED, a laser light source, or a combination of those. In a case where the white light source is a combination of RGB laser light sources, an output intensity and an output timing of each color (each wavelength) can be controlled with high accuracy. Therefore, the light source device 11203 can adjust a white balance of the imaged image. Furthermore, in this case, by irradiating the object to be observed with laser light from each of the RGB laser light sources in time division and controlling the drive of the imaging element of the camera head 11102 in synchronization with the irradiation timing, images respectively corresponding to the R, G, and B can be imaged in time division. According to this method, a color image can be obtained without providing a color filter in the imaging element.

Furthermore, the drive of the light source device 11203 may be controlled so as to change the intensity of output light for each predetermined time period. By controlling the drive of the imaging element of the camera head 11102 in synchronization with a timing of the change of the light intensity and obtaining the images in time division, and synthesizing the images, an image with a high dynamic range that does not have so-called blown-out highlights and blocked up shadows can be generated.

Furthermore, the light source device 11203 may be formed to be capable of supplying light in a predetermined wavelength band compatible with special light observation. In the special light observation, for example, by irradiating light with a narrower band than irradiation light (that is, white light) at the time of normal observation using wavelength dependency of a body tissue to absorb light, so-called Narrow Band Imaging is performed, in which a predetermined tissue such as a blood vessel in a mucosal surface layer is imaged with high contrast. Alternatively, in the special light observation, fluorescence observation for obtaining an image with fluorescence generated by irradiating excitation light may be performed. In fluorescence observation, the fluorescence from the body tissue can be observed by irradiating the body tissue with the excitation light (self-fluorescence observation), or it is possible to inject a reagent such as indocyanine green (ICG) in the body tissue and irradiate the body tissue with the excitation light corresponding to the fluorescence wavelength of the reagent to obtain a fluorescent image. The light source device 11203 can supply narrow band light and/or excitation light compatible with such special light observation.

Figure 14:
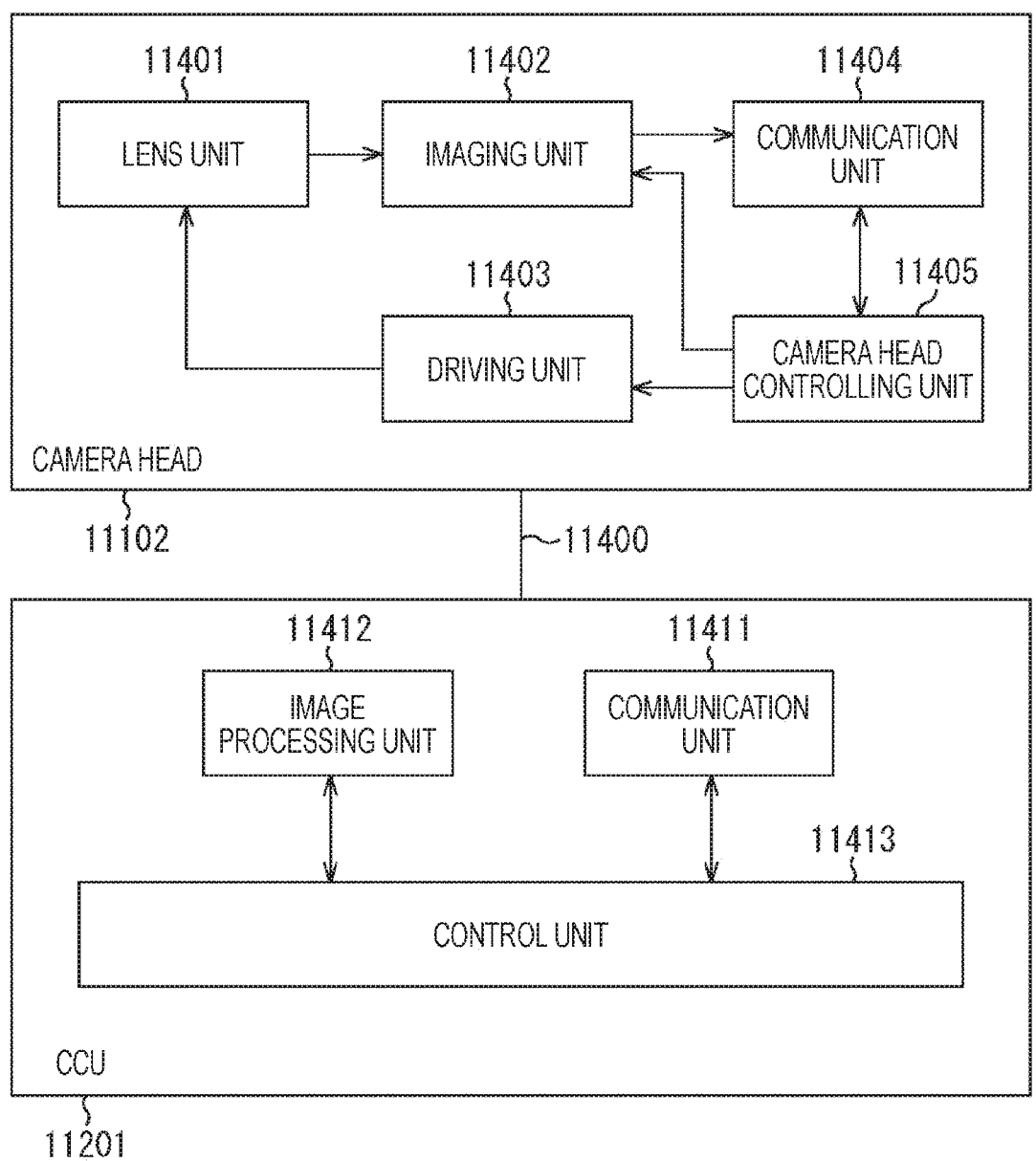
FIG. 14 is a block diagram of an exemplary functional configuration of a camera head and a CCU.

FIG. 14 is a block diagram of an exemplary functional configuration of the camera head 11102 and the CCU 11201 illustrated in FIG. 13.

The camera head 11102 includes a lens unit 11401, an imaging unit 11402, a driving unit 11403, a communication unit 11404, and a camera head controlling unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided at a connecting portion with the lens barrel 11101. Observation light taken from the front end of the lens barrel 11101 is guided to the camera head 11102 and enters the lens unit 11401. The lens unit 11401 is formed by combining a plurality of lenses including zoom lenses and focus lenses.

The imaging unit 11402 is configured of an imaging element. The number of imaging elements forming the imaging unit 11402 may be one (so-called single plate type) or may be plural (so-called multi-plate type). In a case where the imaging unit 11402 has a multi-plate type structure, for example, it is possible that each imaging element generates image signals respectively corresponding to R, G, and B and the image signals are synthesized to obtain a color image. Alternatively, the imaging unit 11402 may include a pair of imaging elements to obtain image signals for the right eye and the left eye coping with three Dimensional (D) display. With the 3D display, the operator 11131 can more accurately recognize the depth of living tissue in the surgical site. Note that in a case where the imaging unit 11402 has a multi-plate type structure, a plurality of lens units 11401 may be provided in correspondence with the imaging elements.

Furthermore, the imaging unit 11402 is not necessarily provided in the camera head 11102. For example, the imaging unit 11402 may be provided just behind the objective lens in the lens barrel 11101.

The driving unit 11403 includes an actuator and moves the zoom lens and the focus lens of the lens unit 11401 by a predetermined distance along an optical axis under the control by the camera head controlling unit 11405. With this movement, the magnification and the focus of the image imaged by the imaging unit 11402 may be appropriately adjusted.

The communication unit 11404 includes a communication device to transmit and receive various information to/from the CCU 11201. The communication unit 11404 transmits the image signal obtained from the imaging unit 11402 to the CCU 11201 via the transmission cable 11400 as RAW data.

Furthermore, the communication unit 11404 receives the control signal to control the drive of the camera head 11102 from the CCU 11201 and supplies the control signal to the camera head controlling unit 11405. The control signal includes, for example, information regarding the imaging condition such as information specifying the frame rate of the imaged image, information specifying the exposure value at the time of imaging, and/or information specifying the magnification and the focus of the imaged image.

Note that the imaging conditions such as the frame rate, the exposure value, the magnification, and the focus may be appropriately specified by a user and may be automatically set by the control unit 11413 of the CCU 11201 on the basis of the obtained image signal. In a case where the imaging condition is automatically set, the endoscope 11100 has a so-called Auto Exposure (AE) function, an Auto Focus (AF) function, and an Auto White Balance (AWB) function.

The camera head controlling unit 11405 controls the drive of the camera head 11102 on the basis of the control signal received from the CCU 11201 via the communication unit 11404.

The communication unit 11411 includes a communication device to transmit and receive various information to/from the camera head 11102. The communication unit 11411 receives the image signal transmitted from the camera head 11102 via the transmission cable 11400.

In addition, the communication unit 11411 transmits the control signal to control the drive of the camera head 11102 to the camera head 11102. The image signal and the control signal can be transmitted through electric communication, optical communication, and the like.

The image processing unit 11412 performs various image processing on the image signal that is the RAW data transmitted from the camera head 11102.

The control unit 11413 performs various control relating to imaging of the surgical site and the like by the endoscope 11100 and display of the imaged image obtained by imaging the surgical site and the like. For example, the control unit 11413 generates the control signal to control the drive of the camera head 11102.

Furthermore, the control unit 11413 makes the display device 11202 display the imaged image of the surgical site and the like on the basis of the image signal to which the image processing has been performed by the image processing unit 11412. In this case, the control unit 11413 may recognize various objects in the imaged image by using various image recognition technologies. For example, by detecting an edge shape, a color, and the like of the object included in the imaged image, the control unit 11413 can recognize a surgical tool such as a forceps, a specific body portion, bleed, mist at the time of using the energy treatment instrument 11112, and the like. When making the display device 11202 display the imaged image, the control unit 11413 may superimpose and display various surgery assist information regarding the image of the surgical site by using the recognition result. The surgery assist information is superimposed and displayed, and is presented to the operator 11131 so that a load of the operator 11131 can be reduced and the operator 11131 can reliably proceed surgery.

The transmission cable 11400 for connecting the camera head 11102 and the CCU 11201 is an electric signal cable compatible with electric signal communication, an optical fiber compatible with optical communication, or a composite cable thereof.

Here, in the illustrated example, wired communication has been performed by using the transmission cable 11400. However, the camera head 11102 and the CCU 11201 may wirelessly communicate with each other.

An example of the endoscopic surgery system to which the technology according to the present disclosure may be applied has been described above. The technology according to the present disclosure can be applied to, for example, the camera head 11102 (imaging unit 11402 thereof) in the above configuration. Specifically, the CMOS image sensor 10 in FIG. 1 can be applied to the imaging unit 11402. By applying the technology according to the present disclosure to the imaging unit 11402, for example, an image of a surgical site with less noise and a wide dynamic range can be obtained. Therefore, the operator can reliably recognize the surgical site.

Note that, although an endoscopic surgery system has been described as an example. However, the technology according to the present disclosure may be applied to, for example, a microscopic surgery system or the like.

[Application to Mobile Body]

In addition, for example, the technology according to the present disclosure (present technology) is realized as an apparatus to be mounted on any type of mobile body such as a car, an electric vehicle, a hybrid electric vehicle, a motorcycle, a bicycle, a personal mobility, an airplane, a drone, a ship, and a robot.

Figure 15:
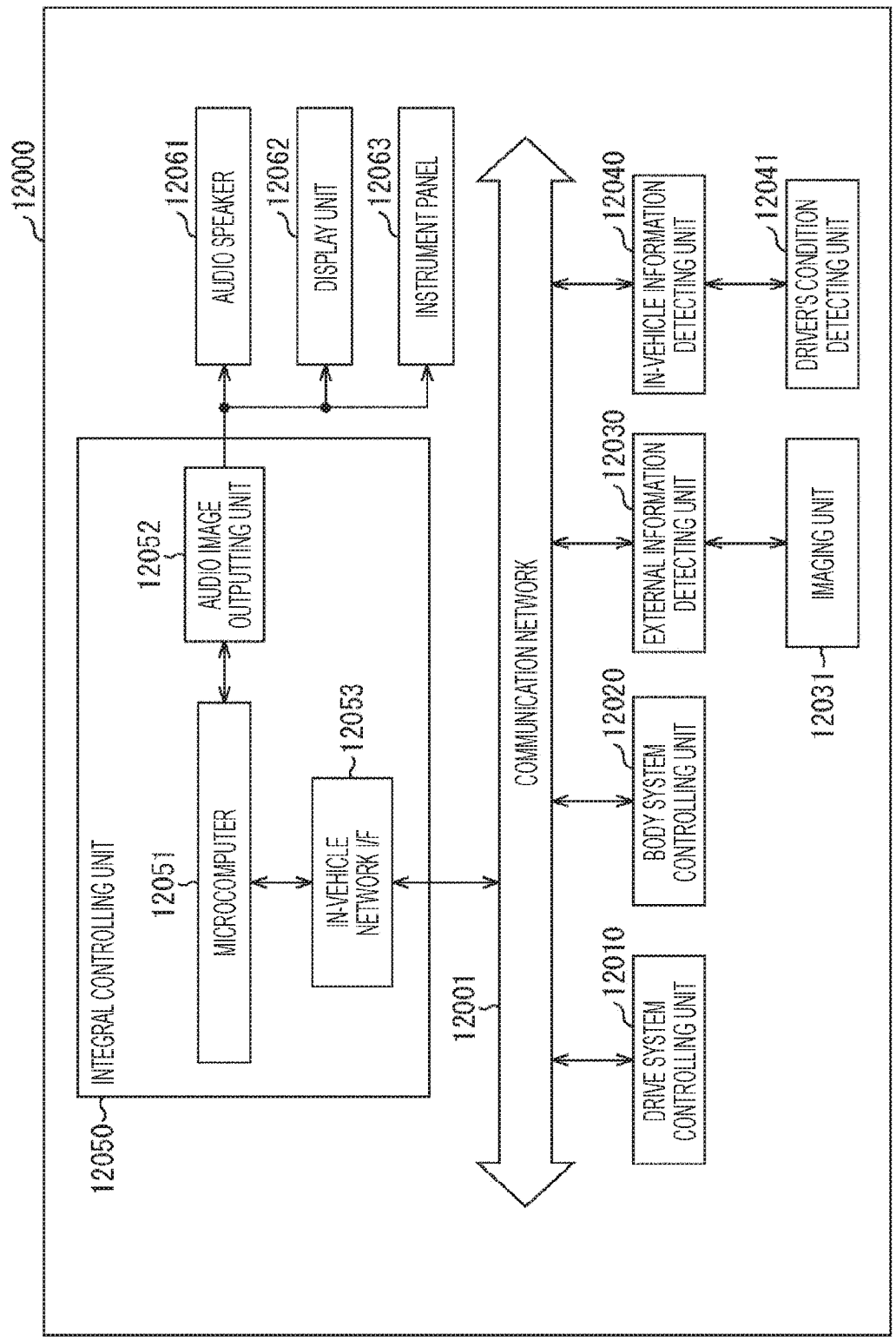
FIG. 15 is a block diagram of an exemplary schematic configuration of a vehicle control system.

FIG. 15 is a block diagram of an exemplary schematic configuration of a vehicle control system which is an example of a mobile body control system to which the technology according to the present disclosure may be applied.

A vehicle control system 12000 includes a plurality of electronic control units connected via a communication network 12001. In the example illustrated in FIG. 15, the vehicle control system 12000 includes a drive system controlling unit 12010, a body system controlling unit 12020, an external information detecting unit 12030, an in-vehicle information detecting unit 12040, and an integral controlling unit 12050. Furthermore, as a functional configuration of the integral controlling unit 12050, a microcomputer 12051, an audio image outputting unit 12052, and an in-vehicle network interface (I/F) 12053 are illustrated.

The drive system controlling unit 12010 controls an operation of a device relating to a driving system of the vehicle in accordance with various programs. For example, the drive system controlling unit 12010 functions as a control device of a device such as a driving force generating device to generate a driving force of the vehicle such as an internal combustion engine or a driving motor, a driving force transmitting mechanism to transmit the driving force to wheels, a steering mechanism which adjusts a steering angle of the vehicle, and a braking device which generates a braking force of the vehicle.

The body system controlling unit 12020 controls operations of various devices attached to the vehicle body in accordance with various programs. For example, the body system controlling unit 12020 functions as a control device of a keyless entry system, a smart key system, a power window device, or various lamps such as a head lamp, a back lamp, a brake lamp, a direction indicator, or a fog lamp. In this case, a radio wave transmitted from a portable machine for substituting a key or signals of various switches may be input to the body system controlling unit 12020. The body system controlling unit 12020 receives the input of the radio wave or the signal and controls a door locking device of the vehicle, the power window device, the lamp, and the like.

The external information detecting unit 12030 detects external information of the vehicle including the vehicle control system 12000. For example, the external information detecting unit 12030 is connected to an imaging unit 12031. The external information detecting unit 12030 makes the imaging unit 12031 image an image outside the vehicle and receives the imaged image. The external information detecting unit 12030 may perform processing of detecting an object such as a human, a car, an obstacle, a sign, or letters on the road or distance detection processing on the basis of the received image.

The imaging unit 12031 is an optical sensor which receives light and outputs an electric signal according to an amount of received light. The imaging unit 12031 can output the electric signal as an image or output the electric signal as information for distance measurement. Furthermore, the light received by the imaging unit 12031 may be visible light or invisible light such as infrared light.

The in-vehicle information detecting unit 12040 detects in-vehicle information. The in-vehicle information detecting unit 12040 is connected to, for example, a driver's condition detecting unit 12041 for detecting a condition of a driver. The driver's condition detecting unit 12041 includes, for example, a camera which images the driver. On the basis of the detection information input by the driver's condition detecting unit 12041, the in-vehicle information detecting unit 12040 may calculate a fatigue degree or a concentration degree of the driver and may determine whether the driver falls asleep.

For example, the microcomputer 12051 can calculate a control target value of the driving force generating device, the steering mechanism, or the braking device on the basis of information inside and outside the vehicle obtained by the external information detecting unit 12030 or the in-vehicle information detecting unit 12040 and can output a control instruction to the drive system controlling unit 12010. For example, the microcomputer 12051 can perform cooperative control to realize a function of an Advanced Driver Assistance System (ADAS) including collision avoidance or impact relaxation of the vehicle, a following travel based on a distance between vehicles, a vehicle speed maintaining travel, a vehicle collision warning, a lane deviation warning of the vehicle, or the like.

In addition, the microcomputer 12051 controls the driving force generating device, the steering mechanism, the braking device, or the like on the basis of the information regarding the surroundings of the vehicle obtained by the external information detecting unit 12030 or the in-vehicle information detecting unit 12040 so as to perform cooperative control for automatic drive in which the vehicle autonomously travels without depending on an operation by the driver and the like.

In addition, the microcomputer 12051 can output a control instruction to the body system controlling unit 12020 on the basis of the information of the outside of the vehicle obtained by the external information detecting unit 12030. For example, the microcomputer 12051 controls the headlamps according to a position of a preceding vehicle or an oncoming vehicle detected by the external information detecting unit 12030 so as to perform cooperative control to prevent a glare such as switching a high beam to a low beam.

The audio image outputting unit 12052 transmits an output signal which is at least one of a voice or an image to an output device which can visually or auditorily notify information of the occupant of the vehicle or the outside the vehicle. In the example in FIG. 15, an audio speaker 12061, a display unit 12062, and an instrument panel 12063 are exemplified as the output device. The display unit 12062 may include, for example, at least one of an on-board display and a head-up display.

Figure 16:
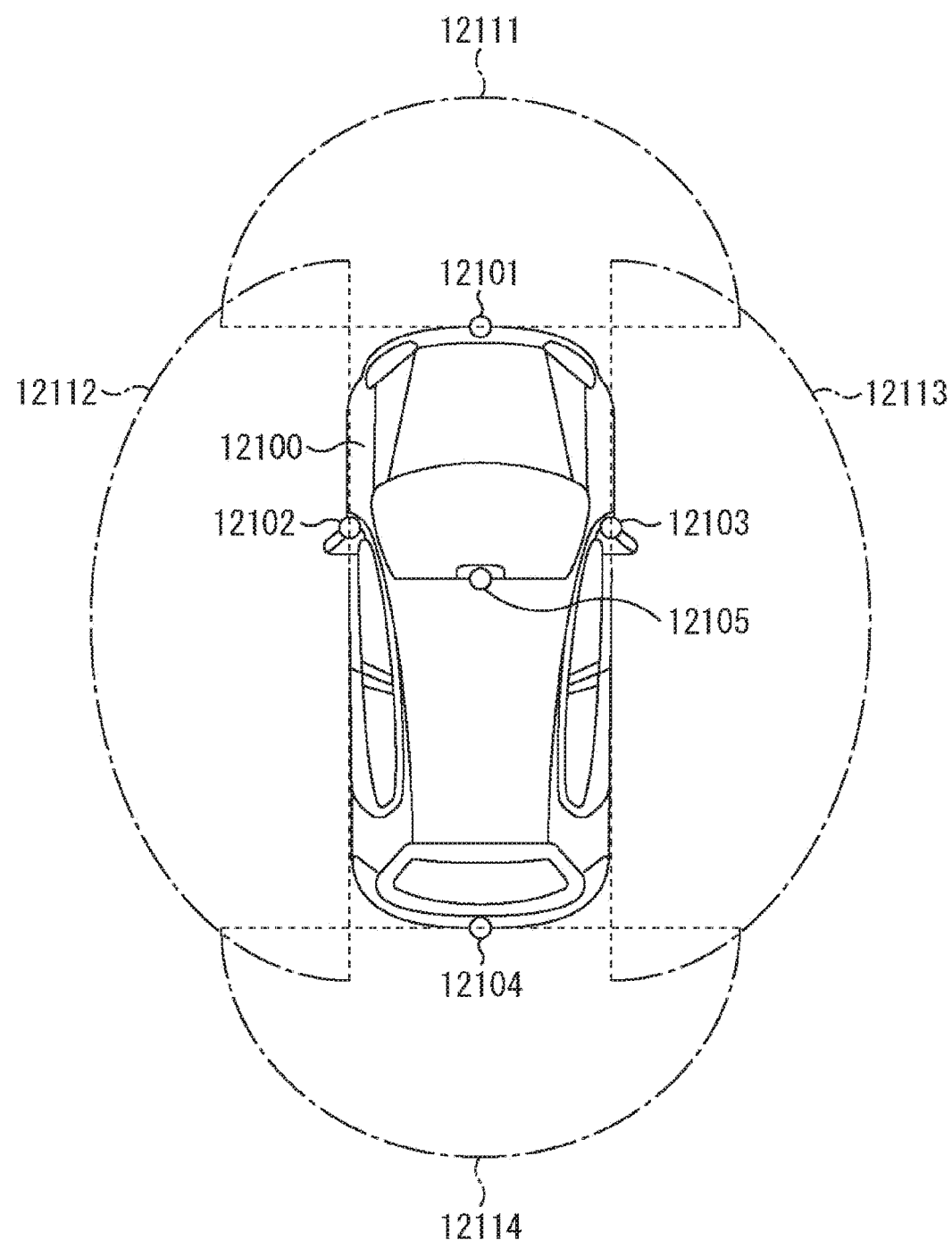
FIG. 16 is an explanatory diagram of exemplary set positions of an external information detecting unit and imaging units.

FIG. 16 is an explanatory diagram of an exemplary set position of the imaging units 12031.

In FIG. 16, a vehicle 12100 includes imaging units 12101, 12102, 12103, 12104, and 12105 as an imaging unit 12031.

Each of the imaging units 12101, 12102, 12103, 12104, and 12105 is provided in one of, for example, a front nose, a side mirror, a rear bumper, a back door, an upper side of a windshield in a vehicle interior of a vehicle 12100, and the like. The imaging unit 12101 provided in the front nose and the imaging unit 12105 provided on the upper side of the windshield in the vehicle interior mainly obtain images on front side of the vehicle 12100. The imaging units 12102 and 12103 provided in the side mirrors mainly obtain images on the sides of the vehicle 12100. The imaging unit 12104 provided in the rear bumper or the back door mainly obtains an image on the back side of the vehicle 12100. The image on the front side obtained by the imaging units 12101 and 12105 is mainly used to detect a preceding vehicle, a pedestrian, an obstacle, a traffic signal, a traffic sign, a lane, or the like.

It should be noted that, in FIG. 16, exemplary imaging ranges of the imaging units 12101 to 12104 are illustrated. An imaging range 12111 indicates an imaging range of the imaging unit 12101 provided in the front nose, and imaging ranges 12112 and 12113 respectively indicate imaging ranges of the imaging units 12102 and 12103 provided in the side mirrors. An imaging range 12114 indicates an imaging range of the imaging unit 12104 provided in the rear bumper or the back door. For example, image data imaged by the imaging units 12101 to 12104 is superposed so that a bird's-eye image of the vehicle 12100 viewed from above can be obtained.

At least one of the imaging units 12101 to 12104 may have a function of obtaining distance information. For example, at least one of the imaging units 12101 to 12104 may be a stereo camera including a plurality of imaging elements or may be an imaging element having pixels to detect a phase difference.

For example, by obtaining a distance to solid objects in the respective imaging ranges 12111 to 12114 and a temporal change of the distance (relative speed to vehicle 12100) on the basis of the distance information obtained from the imaging units 12101 to 12104, the microcomputer 12051 can extract a solid object which is positioned on a traveling route of the vehicle 12100 and positioned closest to the vehicle 12100 and travels at a predetermined speed (for example, equal to or more than 0 km/h) in a direction substantially the same as the direction in which the vehicle 12100 travels, as a preceding vehicle. In addition, the microcomputer 12051 can set a distance between the vehicles which should be previously secured in front of the preceding vehicle and perform automatic brake control (including following travel stop control), automatic acceleration control (including following travel start control), and the like. In this way, the cooperative control can be performed for automatic drive and the like in which the vehicle autonomously travels without depending on the operation by the driver.

For example, on the basis of the distance information obtained from the imaging units 12101 to 12104, the microcomputer 12051 can classify solid object data regarding the solid object into a two-wheeled vehicle, a regular vehicle, a large vehicle, a pedestrian, a utility pole, and other solid object and extract the data so as to use the extracted data to automatically avoid an obstacle. For example, the microcomputer 12051 identifies an obstacle around the vehicle 12100 into an obstacle which can be visually recognized by the driver of the vehicle 12100 and an obstacle which is hard to be visually recognized by the driver. Then, the microcomputer 12051 determines a collision risk indicating a danger of risk of the collision with each obstacle. When the collision risk is equal to or higher than a predetermined value and the vehicle may collide the obstacle, the microcomputer 12051 can assist driving to avoid collision by outputting a warning to the driver via the audio speaker 12061 and the display unit 12062 or by forcing deceleration or steering to avoid the obstacle via the drive system controlling unit 12010.

At least one of the imaging units 12101 to 12104 may be an infrared camera for detecting infrared light. For example, the microcomputer 12051 can recognize a pedestrian by determining whether the pedestrian exists in the imaged images of the imaging units 12101 to 12104. The pedestrian is recognized, for example, by a procedure of extracting feature point points in the imaged images of the imaging units 12101 to 12104 as the infrared cameras and a procedure of performing pattern matching processing on the series of feature points indicating the shape of the object to determine whether the object is a pedestrian. When the microcomputer 12051 determines that the pedestrian exists in the imaged images of the imaging units 12101 to 12104 and recognizes the pedestrian, the audio image outputting unit 12052 controls the display unit 12062 to display superimposed rectangular outlines to emphasize the recognized pedestrian. Furthermore, the audio image outputting unit 12052 may control the display unit 12062 to display an icon and the like indicating the pedestrian at a desired position.

An example of the vehicle control system to which the technology according to the present disclosure may be applied has been described above. The technology according to the present disclosure may be applied to, for example, the imaging unit 12031 in the above configuration. Specifically, for example, the CMOS image sensor 10 in FIG. 1 can be applied to the imaging unit 12031. By applying the technology according to the present disclosure to the imaging unit 12031, for example, an imaged image with less noise and a wide dynamic range can be obtained. Therefore, the object around the vehicle can be more accurately detected.

Furthermore, the embodiment of the present technology is not limited to the above-mentioned embodiment, and various changes can be made without departing from the scope of the present technology.

Furthermore, for example, the present technology can have the configuration below.

(1) An imaging element including:
a pixel array unit in which pixels respectively having charge voltage converting units and switches are arranged, in which
the charge voltage converting units of the plurality of pixels are connected to a signal line in parallel via the respective switches.

(2) The imaging element according to (1), in which the signal line extends in a direction in which the pixels are aligned in the pixel array unit.

(3) The imaging element according to (1) or (2), in which in the pixel, pixel transistors are substantially symmetrically arranged in at least one direction of alignment directions of the pixels in the pixel array unit.

(4) The imaging element according to (3), in which the pixel includes a plurality of photoelectric conversion elements and a plurality of transfer transistors that transfers an electric charge generated by each photoelectric conversion element to the charge voltage converting unit, and
in the pixel, the plurality of transfer transistors is substantially symmetrically arranged in the same direction as the pixel transistors.

(5) The imaging element according to (3) or (4), in which the pixel transistor includes a reset transistor used to reset the charge voltage converting unit, an amplification transistor used to amplify a voltage of the charge voltage converting unit, and a coupling transistor configuring the switch.

(6) The imaging element according to (5), in which the pixel transistor further includes a selection transistor used to select the pixel.

(7) An electronic device including:
an imaging element including a pixel array unit in which pixels respectively having charge voltage converting units and switches are arranged, and in which, charge voltage converting units of the plurality of pixels are connected to a signal line in parallel via the respective switches; and
a signal processing unit configured to perform processing on a signal of the imaging element.

REFERENCE SIGNS LIST

10 CMOS image sensor
11 pixel array unit
12 vertical driving unit
13 column processing unit
14 horizontal driving unit
15 system controlling unit
16 pixel driving line
17 vertical signal line
18 signal processing unit
51*a* to 51*d* pixel
61, 61-1, 61-2, 61*a*-1 to 61*a*-4, 61*b*-1 to 61*b*-4 photoelectric conversion element
62, 62-1, 62-2, 62*a*-1 to 62*a*-4, 62*b*-1 to 62*b*-4 transfer gate unit
63, 63*a*, 63*b* charge voltage converting unit
64 reset transistor
65 amplification transistor
66 selection transistor
67 coupling transistor
68 power supply line
69 capacitance coupling line
101, 102*a*, 102*b*, 103 contact hole
200 electronic device
202 imaging element
203 DSP circuit

The invention claimed is:

1. An imaging element, comprising:
a pixel array unit that comprises:
a plurality of pixels;
a plurality of charge voltage converting units; and
a plurality of switches, wherein
a pixel of the plurality of pixels comprises:
a charge voltage converting unit of the plurality of charge voltage converting units;
a plurality of pixel transistors that includes an amplification transistor, a selection transistor, a reset transistor, and a coupling transistor;
a plurality of transfer gate units;
a plurality of photoelectric conversion elements, wherein
the plurality of transfer gate units and the plurality of photoelectric conversion elements are in a substantially symmetrical arrangement, around the charge voltage converting unit, in a vertical direction of alignment of the plurality of pixels in the pixel array unit and a horizontal direction of the alignment of the plurality of pixels in the pixel array unit; and
a switch of the plurality of switches, wherein
the reset transistor and the coupling transistor are on a first side of the charge voltage converting unit,
the selection transistor and the amplification transistor are on a second side of the charge voltage converting unit,
the first side is different from the second side,
each of the reset transistor, the coupling transistor, the selection transistor, and the amplification transistor is connected to the charge voltage converting unit, and
the plurality of charge voltage converting units is connected to a signal line in parallel via respective switches of the plurality of switches.

2. The imaging element according to claim 1, wherein the signal line extends in the vertical direction of the alignment of the plurality of pixels in the pixel array unit.

3. The imaging element according to claim 1, wherein each pixel of the plurality of pixels comprises the plurality of pixel transistors in a substantially symmetrical arrangement in at least one direction of a plurality of alignment directions of the plurality of pixels in the pixel array unit.

4. The imaging element according to claim 3, wherein each pixel of the plurality of pixels further comprises:
the plurality of photoelectric conversion elements, wherein
each photoelectric conversion element of the plurality of photoelectric conversion elements is configured to generate an electric charge; and
the plurality of transfer gate units, wherein
each transfer gate unit of the plurality of transfer gate units is configured to transfer the electric charge, generated by a respective photoelectric conversion element of the plurality of photoelectric conversion elements, to a respective charge voltage converting unit of the plurality of charge voltage converting units.

5. The imaging element according to claim 3, wherein
the reset transistor is configured to reset a respective charge voltage converting unit of the plurality of charge voltage converting units,
the amplification transistor is configured to amplify a voltage of the respective charge voltage converting unit; and
the coupling transistor constitutes a respective switch of the plurality of switches.

6. The imaging element according to claim 5, wherein the selection transistor is configured to select a respective pixel of the plurality of pixels.

7. An electronic device, comprising:
an imaging element comprising a pixel array unit, wherein the pixel array unit comprises:
a plurality of pixels;
a plurality of charge voltage converting units; and
a plurality of switches, wherein
a pixel of the plurality of pixels comprises:
a charge voltage converting unit of the plurality of charge voltage converting units;
a plurality of pixel transistors that includes an amplification transistor, a selection transistor, a reset transistor, and a coupling transistor;
a plurality of transfer gate units;
a plurality of photoelectric conversion elements, wherein
the plurality of transfer gate units and the plurality of photoelectric conversion elements are in a substantially symmetrical arrangement, around the charge voltage converting unit, in a vertical direction of alignment of the plurality of pixels in the pixel array unit and a horizontal direction of the alignment of the plurality of pixels in the pixel array unit; and
a switch of the plurality of switches, wherein
the reset transistor and the coupling transistor are on a first side of the charge voltage converting unit,
the selection transistor and the amplification transistor are on a second side of the charge voltage converting unit,
the first side is different from the second side,
each of the reset transistor, the coupling transistor, the selection transistor, and the amplification transistor is connected to the charge voltage converting unit, and
the plurality of charge voltage converting units is connected to a signal line in parallel via respective switches of the plurality of switches; and
a signal processing unit configured to process a signal of the imaging element.

* * * * *